(12) United States Patent
Wright et al.

(10) Patent No.: US 12,125,560 B2
(45) Date of Patent: Oct. 22, 2024

(54) PHENOTYPE MEASUREMENT SYSTEMS AND METHODS

(71) Applicant: FenoLogica Biosciences, Inc., Seattle, WA (US)

(72) Inventors: Matthew Ian Wright, Auburn, WA (US); Adrian Christopher Scott, Deming, WA (US); Sean Matthew MacLeod, Seattle, WA (US); Megan Lew Kuhn, Seattle, WA (US)

(73) Assignee: FenoLogica Biosciences, Inc., Seattle, WA (US)

( * ) Notice: Subject to any disclaimer, the term of this patent is extended or adjusted under 35 U.S.C. 154(b) by 0 days.

(21) Appl. No.: 18/078,803

(22) Filed: Dec. 9, 2022

(65) Prior Publication Data

US 2023/0360735 A1     Nov. 9, 2023

Related U.S. Application Data

(63) Continuation of application No. 16/489,672, filed as application No. PCT/US2018/020794 on Mar. 2, 2018, now abandoned.
(Continued)

(51) Int. Cl.
    *G16B 40/30*     (2019.01)
    *C12M 1/36*     (2006.01)
(Continued)

(52) U.S. Cl.
    CPC ............ *G16B 40/30* (2019.02); *C12M 41/48* (2013.01); *G06V 20/695* (2022.01);
(Continued)

(58) Field of Classification Search
None
See application file for complete search history.

(56) References Cited

U.S. PATENT DOCUMENTS

| 5,287,272 A | 2/1994 | Rutenberg et al. |
| 5,694,478 A | 12/1997 | Braier et al. |

(Continued)

FOREIGN PATENT DOCUMENTS

| WO | WO-2018161052 A1 | 9/2018 |
| WO | WO-2019014151 A1 | 1/2019 |

OTHER PUBLICATIONS

Baba et al.: Construction of *Escherichia coli* K-12 in-frame, single-gene knockout mutants: the Keio collection. Mol Syst Biol. 2006;2:2006.0008. Epub Feb. 21, 2006.
(Continued)

*Primary Examiner* — Delomia L Gilliard
(74) *Attorney, Agent, or Firm* — Wilson Sonsini Goodwich & Rosati

(57) ABSTRACT

An image acquisition and analysis system are disclosed. The system enables high throughput, objective analysis of microbial samples over days or weeks. The system may accommodate upwards of twelve 96- or 384-well plates simultaneously (liquid or solid media). The system may acquire and analyze a large number of samples in a short period of time. For example, over 384 samples per minute or 18,432 samples per hour. The system hardware may include a multi-spectral imager (fluorescence and bright field detection), electro-mechanical assemblies, and an optional high-resolution stage. The system may automate image acquisition, image data processing, simplify data storage, and enable automated analysis tools to significantly reduce the manual labor and time associated with such tasks. The system may allow for quick processing and analysis of data into clear phenotypic classes. The analysis capabilities may include colony growth, colorimetry, and structural morphology assays, and automated phenotype classification capabilities.

20 Claims, 7 Drawing Sheets

Related U.S. Application Data

(60) Provisional application No. 62/467,011, filed on Mar. 3, 2017.

(51) Int. Cl.
- G01N 15/10 (2024.01)
- G01N 15/1429 (2024.01)
- G01N 15/1433 (2024.01)
- G06V 20/69 (2022.01)
- G16B 45/00 (2019.01)
- G16H 10/40 (2018.01)
- G16H 30/40 (2018.01)

(52) U.S. Cl.
CPC .......... *G06V 20/698* (2022.01); *G16B 45/00* (2019.02); *G16H 10/40* (2018.01); *G01N 2015/1006* (2013.01); *G01N 15/1429* (2013.01); *G01N 15/1433* (2024.01); *G16H 30/40* (2018.01)

(56) References Cited

U.S. PATENT DOCUMENTS

| | | | |
|---|---|---|---|
| 6,046,021 | A | 4/2000 | Bochner |
| 6,716,588 | B2 | 4/2004 | Sammak et al. |
| 7,796,815 | B2 | 9/2010 | Muschler et al. |
| 7,920,736 | B2 * | 4/2011 | Sammak .............. G06V 10/764 382/133 |
| 9,275,265 | B2 | 3/2016 | Deppermann et al. |
| 2001/0048899 | A1 | 12/2001 | Marouiss et al. |
| 2003/0108450 | A1 | 6/2003 | Mainquist et al. |
| 2006/0039593 | A1 | 2/2006 | Sammak et al. |
| 2007/0248976 | A1 | 10/2007 | Harding |
| 2008/0014571 | A1 | 1/2008 | Teich et al. |
| 2008/0279441 | A1 | 11/2008 | Matsuo et al. |
| 2013/0189671 | A1 | 7/2013 | Hoh et al. |
| 2017/0121759 | A1 | 5/2017 | Jarvius et al. |
| 2019/0385707 | A1 * | 12/2019 | Wright ............... G01N 15/0612 |
| 2020/0131459 | A1 | 4/2020 | Baum et al. |

OTHER PUBLICATIONS

Balouiri et al.: Methods for in vitro evaluating antimicrobial activity: A review. J Pharm Anal. 6(2): 71-79 (2016).
Barr et al.: Serial image analysis of Mycobacterium tuberculosis colony growth reveals a persistent subpopulation in sputum during treatment of pulmonary TB. Tuberculosis (Edinb). 98:110-115 (2016).
Baryshnikova et al.: Quantitative analysis of fitness and genetic interactions in yeast on a genome scale. Nat Methods. 7(12): 1017-1024 (2010).
Bischof et al.: Spotsizer: High-throughput quantitative analysis of microbial growth. Biotechniques 61(4): 191-201 (2017) 14 pages.
Blomberg, A.: Measuring growth rate in high-throughput growth phenotyping. Curr Opin Biotechnol. 22(1): 94-102 (2011).
Boggs et al.: Antibacterial drug discovery: is small pharma the solution? Clin Microbiol Infect. 10 Suppl 4: 32-36 (2004).
Buchan et al.: Emerging technologies for the clinical microbiology laboratory. Clin Microbiol Rev. 27(4): 783-822 (2014).
Choudhry, P.: High-Throughput Method for Automated Colony and Cell Counting by Digital Image Analysis Based on Edge Detection. PLoS One. 11(2): e0148469. 23 pages (2016).
Cobb et al.: Next-generation phenotyping: requirements and strategies for enhancing our understanding of genotype-phenotype relationships and its relevance to crop improvement. Theor Appl Genet. 126(4): 867-887 (2013).
Costanzo et al.: A global genetic interaction network maps a wiring diagram of cellular function. Science. 353(6306) 34 pages (2016).
Costerton et al.: Bacterial biofilms: a common cause of persistent infections. Science 284:1318-1322 (1999).
Cromie et al.: Genomic sequence diversity and population structure of *Saccharomyces cerevisiae* assessed by RAD-seq. G3 (Bethesda). 3(12): 2163-2171 (2013).
Den Hertog et al.: Simplified automated image analysis for detection and phenotyping of Mycobacterium tuberculosis on porous supports by monitoring growing microcolonies. PLoS One. 5(6): e11008. 8 pages (2010).
Dittmar et al.: ScreenMill: A freely available software suite for growth measurement, analysis and visualization of high-throughput screen data. BMC Bioinformatics 11:353 (2010) 11 pages.
Dudley et al.: A global view of pleiotropy and phenotypically derived gene function in yeast. Molecular Systems Biology. 1-11 (2005).
Dudley et al.: Specific components of the SAGA complex are required for Gcn4- and Gcr1-mediated activation of the his4-912delta promoter in *Saccharomyces cerevisiae*. Genetics. 151(4): 1365-1378 (1999).
Eifler et al.: A screening protocol for identification of functional mutants of RNA editing adenosine deaminases. Curr Protoc Chem Biol. 4(4): 357-369 (2012).
Fuxman et al.: Colony Lift Colorimetric Assay for 13-Galactosidase Activity. Cold Spring Harb Protoc 1110-1112. pdb.prot088963 doi:10.1101/pdb.prot088963. (2016).
Giaever et al.: Functional profiling of the *Saccharomyces cerevisiae* genome. Nature. 2002; 418:387-391.
Graham T. Market Report: Global Markets for Microbiology Technology, Equipment, and Consumables. BCC Res 2016: 40-42, 48-49.
Granek et al.: Environmental and genetic determinants of colony morphology in yeast. PLoS Genet. 6(1): e1000823. 12 pages (2010).
Granier et al.: Phenotyping and beyond: modelling the relationships between traits. Curr Opin Plant Biol. 18: 96-102 (2014).
Green et al.: PhenoPhyte: a flexible affordable method to quantify 2D phenotypes from imagery. Plant Methods 8:45, 12 pages (2012).
Griffith et al.: Measuring beta-galactosidase activity in bacteria: cell growth, permeabilization, and enzyme assays in 96-well arrays. Biochem Biophys Res Commun. 290(1): 397-402 (2002).
Ha et al.: Impact of first-line antifungal agents on the outcomes and costs of candidemia. Antimicrob Agents Chemother. 56(7): 3950-3956 (2012).
Hope et al.: Ploidy-regulated variation in biofilm-related phenotypes in natural isolates of *Saccharomyces cerevisiae*. G3 (Bethesda). 4(9): 1773-1786 (2014).
Houle et al.: Phenomics: the next challenge. Nat Rev Genet. 11(12): 855-866 (2010).
International search report with written opinion dated Sep. 12, 2018 for PCT/US18/41342.
Jin et al.: Large-scale analysis of yeast filamentous growth by systematic gene disruption and overexpression. Mol Biol Cell. 19(1): 284-296 (2008).
Kritikos et al.: A tool named Iris for versatile high-throughput phenotyping in microorganisms. Nature Microbiology 2(17014): 1-10 (2017).
Kuthan et al.: Domestication of wild *Saccharomyces cerevisiae* is accompanied by changes in gene expression and colony morphology. Mol Microbiol. 47(3): 745-754 (2003).
Ledeboer et al.: The automated clinical microbiology laboratory: fact or fantasy? J Clin Microbiol. 52(9): 3140-3146 (2014).
Lee et al.: Phenotypic diversity and genotypic flexibility of Burkholderia cenocepacia during long-term chronic infection of cystic fibrosis lungs. Genome Res. 27(4): 650-662 (2017).
Levin-Reisman et al.: Automated imaging with ScanLag reveals previously undetectable bacterial growth phenotypes. Nature Methods 7(9): 737-741 (2010).
Otsu. A Threshold Selection Method from Gray-Level Histograms. Systems, Man and Cybernetics, IEEE Transactions on 9(1), 62-66 (1979).
Padilla-Vaca et al.: Synthetic biology: Novel approaches for microbiology. Int Microbiol. 18(2): 71-84 (2015).
Pendrak et al.: Hbr1 Activates and Represses Hyphal Growth in Candida albicans and Regulates Fungal Morphogenesis under Embedded Conditions. PLoS One. 10(6): e0126919. 22 pages (2015).

(56) References Cited

OTHER PUBLICATIONS

Roemer et al.: Antifungal drug development: challenges, unmet clinical needs, and new approaches. Cold Spring Harb Perspect Med. 4(5) 1-14 (2014).
Ruusuvuori et al.: Quantitative analysis of colony morphology in yeast. Biotechniques. 56(1): 18-27 (2014).
Ruusuvuori et al.: Supplementary Material For: Reports—Quantitative analysis of colony morphology in yeast. Biotechniques. 56(1): 18-27 (2014), 8 pages.
Sandai et al.: Resistance of Candida albicans Biofilms to Drugs and the Host Immune System. Jundishapur J Microbiol. 9(11): e37385. 7 pages (2016).
Scheffler et al.: Antimicrobials, drug discovery, and genome mining. Appl Microbiol Biotechnol. 97(3): 969-978 (2013).
Scott et al.: BEST: Barcode Enabled Sequencing of Tetrads. J. Vis. Exp. (87), e51401, (2014) 8 pages.
Sirr et al.: Allelic Variation, Aneuploidy, and Nongenetic Mechanisms Suppress a Monogenic Trait in Yeast. Genetics 199: 247-262 (2015).
Snitkin et al.: Model-driven analysis of experimentally determined growth phenotypes for 465 yeast gene deletion mutants under 16 different conditions. Genome Biol. 9(9): R140. 18 pages (2008).
Stovicek et al.: General factors important for the formation of structured biofilm-like yeast colonies. Fungal Genet Biol. 47(12): 1012-1022 (2010).
Stovicek et al.: Yeast biofilm colony as an orchestrated multicellular organism. Commun Integr Biol. 5(2): 203-205 (2012).
Swinney, D.C.: Phenotypic vs. target-based drug discovery for first-in-class medicines. Clin Pharmacol Ther. 93(4): 299-301 (2013).
Tan et al.: Aneuploidy underlies a multicellular phenotypic switch. Proc Natl Acad Sci U S A. 110(30): 12367-12372 (2013).
Tan et al.: It's not just fluff: mechanisms underlying the ability of *Saccharomyces cerevisiae* to build complex multicellular colonies. A dissertation submitted in partial fulfillment of the requirements for the degree of: Doctor of Philosophy University of Washington (2014) 179 pages.
Xie et al.: N-acetylglucosamine induces white-to-opaque switching and mating in Candida tropicalis, providing new insights into adaptation and fungal sexual evolution. Eukaryot Cell. 11(6): 773-782 (2012).
Zackrisson et al.: Scan-o-matic: High-Resolution Microbial Phenomics at a Massive Scale. G3 Genes Genomes Genetics 6: 3003-3014 (2016).
Zheng et al.: Phenotypic screens as a renewed approach for drug discovery. Drug Discov Today 18(21-22): 1067-1073 (2013).

\* cited by examiner

PHENOTYPE MEASUREMENT SYSTEMS AND METHODS

CROSS REFERENCE

This application is a continuation of U.S. patent application Ser. No. 16/489,672 filed Aug. 28, 2019, which is a U.S. National Phase Application under 35 U.S.C. § 371 of International Application No. PCT/US2018/020794, filed Mar. 2, 2018, which claims the benefit of U.S. Provisional Patent Application No. 62/467,011, filed Mar. 3, 2017, the entire disclosures of which are incorporated by reference.

TECHNICAL FIELD

This disclosure is generally related to the detection and analysis of phenotypes. More particularly, this disclosure is related to the automated detection, analysis, and classification of phenotypes of cellular assays.

BACKGROUND OF THE INVENTION

Current instrumentation for phenotype measurement is not keeping pace with the scale in which modern microbiology and cell molecular biology is performed. Quantitative methodologies are used to study cellular functions, the molecular mechanisms underlying specific phenotypes, and the levels of RNAs, proteins, and metabolites. For example, insights about the virulence or drug resistance of pathogenic bacteria or fungi could be gained from quantitative growth dynamics and morphological analyses of cellular colonies over extended periods of time (days to weeks). However, currently systems only provide for microbial researchers to choose between highly accurate temporal resolution experiments on a relatively small number of strains or conditions, or single end-point data acquisition for a large number of strains or conditions. Furthermore, current systems fail to provide an efficient means of integrating the vast quantities of data produced among a group of experiments or among the combined experiments of a group of collaborating researchers during data analysis.

SUMMARY OF THE INVENTION

An image acquisition and analysis system are disclosed. The system enables high throughput, objective analysis of two-dimensional or three-dimensional cell or colony cultures (including spheroid or organoid cultures) of animal, plant, or microbial samples over days or weeks. The system may accommodate upwards of twelve single-well plates, 96-well plates or 384-well plates simultaneously (liquid or solid media, including agar or other gel matrices). The system may acquire and analyzing a large number of samples in a short period of time. For example, over 384 samples per minute or 18,432 samples per hour. The system hardware may include a multi-spectral imager (fluorescence and bright field detection), electro-mechanical assemblies, system-level and sample-level environmental controls and monitoring, and an optional high-resolution stage. The system may automate image acquisition, image data processing, simplify data storage, and enable automated analysis tools to significantly reduce the manual labor and time associated with such tasks. The system may allow for quick processing and analysis of data into clear phenotypic classes. The analysis capabilities may include colony growth, colorimetry, and structural morphology assays, and user-defined, supervised, or unsupervised automated phenotype classification capabilities.

In various aspects, the present disclosure provides methods and systems for the classification of one or more specimen. In some aspects, the present disclosure provides systems comprising a controller configured to interface with one or more instrument through an instrument gateway module configured to receive one or more experimental data set from the one or more instrument, wherein the one or more experimental data set is produced during one or more experiment extract one or more feature data set from the one or more experimental data set, store at least a portion of the one or more feature data set in a long-term data storage subsystem, store at least a portion of the one or more feature data set or at least a portion of the one or more experimental data set in a short-term storage cache, build one or more classification profile based on a classification data set comprising at least a portion of the one or more feature data set and classify one or more specimen of an experiment of the one or more experiment using the one or more classification profile.

In some aspects, the classification data set comprises at least a portion of each feature data set of a plurality of feature data sets, wherein a first portion of the each feature data set is produced from a first experimental data set and a second portion of the each feature data set is produced from a second experimental data set.

In some aspects of the present disclosure, the first experimental data set comprises data from a different experiment of the one or more experiment than the data of the second experimental data set. In some aspects, the controller receives a plurality of experimental data sets from a plurality of experiments before the extracting is performed on any of the experimental data sets. In some aspects, the controller receives a plurality of experimental data sets from a plurality of experiments before the classifying is performed on any of the experimental data sets. In some embodiments, at least a portion of the first experimental data set is received from a different instrument of the one or more instrument than the second experimental data set. In some respects, the classification of one or more specimen comprises categorizing the one or more specimen based on one or more feature data set. In some aspects, building the classification profile comprises supervised machine learning. In some aspects, building the classification profile comprises unsupervised machine learning. In some aspects, the classification is performed in real-time, near real-time, or batch mode.

In some aspects of the present disclosure, classification results are determined from the classification of one or more specimen of an experiment of the one or more experiment using the classification profile. In some aspects, the controller is further configured to display the classification results in real-time, near real-time, or batch mode. In some aspects, the controller is further configured to display an analysis data set comprising at least a portion of the experimental data set, at least a portion of the feature data set, or at least a portion of the classification data set. In some aspects, the analysis data set is displayed in real-time, near-real time, or batch mode.

In some embodiments of the present disclosure, the experimental data set comprises image data. In some embodiments, the experimental data set comprises a positive file format.

In some embodiments of the present disclosure, the controller is further configured to transmit an experiment design to the one or more instrument.

In some aspects of the present disclosure, the specimen comprises one or more cell. In some aspects, a cell of the one or more cell comprises a genetically modified cell. In some aspects, the specimen comprises a plurality of cells. In some aspects, the plurality of cells comprises a heterogeneous mixture of cells. In some aspects, the plurality of cells comprises one or more colony of cells.

In some embodiments of the present disclosure, an experiment of the one or more experiments comprises an antibiotic screening assay, a drug screening assay, a cellular growth assay, a colony growth assay, a bio-prospecting assay, or an assay correlating molecular expression with functional activity.

In various aspects, the present disclosure provides methods for the classification of one or more specimen, the methods comprising: receiving one or more experimental data set from one or more instrument, wherein the one or more experimental data set is produced during one or more experiment; extracting one or more feature data set from the one or more experimental data set; storing at least a portion of the one or more feature data set in a long-term data storage subsystem; storing at least a portion of the one or more feature data set or at least a portion of the one or more experimental data set in a short-term storage cache; building one or more classification profile based on a classification data set comprising at least a portion of the one or more feature data set; and classifying one or more specimen of an experiment of the one or more experiment using the one or more classification profile.

In some aspects, a plurality of experimental data sets is received before the extracting is performed on any of the experimental data sets of the plurality of experimental data sets. In some aspects, a plurality of experimental data sets is received before the classifying is performed on any of the experimental data sets of the plurality of experimental data sets. In some aspects, the classification of one or more specimen comprises categorizing the one or more specimen based on one or more set of feature data. In some aspects, building the classification profile comprises supervised machine learning. In some aspects, building the classification profile comprises unsupervised machine learning. In some aspects, the present disclosure provides methods comprising displaying an analysis data set comprising at least a portion of the experimental data set, at least a portion of the feature data set, or at least a portion of the classification data set. In some respects, the classification results are displayed in real-time, near real-time, or batch mode. In some aspects, the present disclosure provides methods further comprising displaying an analysis data set comprising at least a portion of the experimental data set, at least a portion of the feature data set, or at least a portion of the classification data set. In some aspects, the present disclosure provides methods further comprising transmitting an experiment design to the one or more instrument.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
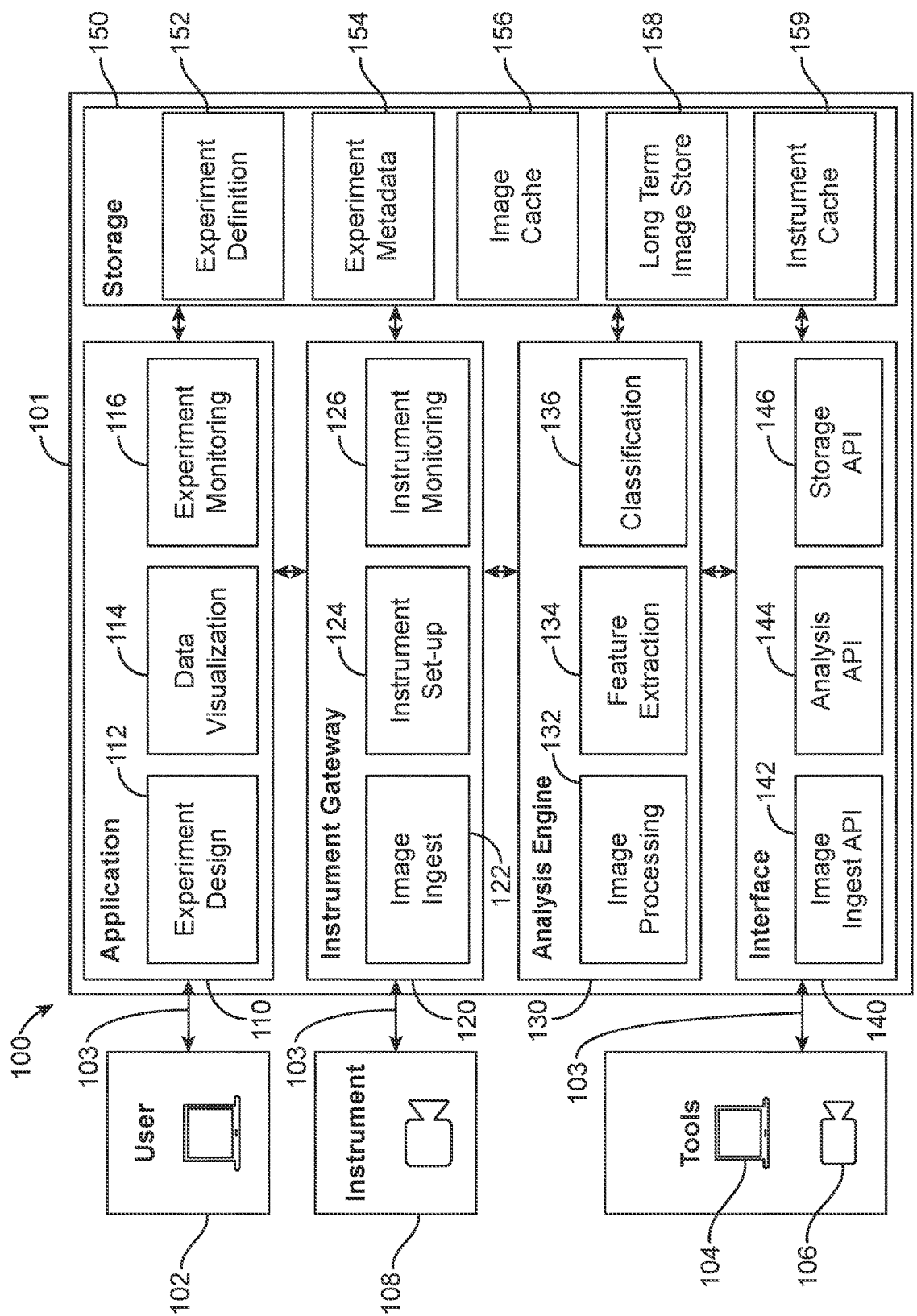
FIG. 1 shows a block diagram of a system for integrated high-throughput phenotypic analysis of cellular assay data and associated data flow in accordance with one or more embodiments disclosed herein.

The systems, methods, and devices described herein can be used to automatically and efficiently process experimental data from one or more experiment. In some embodiments, these systems, methods, and devices can be configured to coordinate and perform analysis and classification of massive data sets received from a plurality of data acquisition tools. For example, the systems, methods, and devices described herein can be used to automatically extract a customizable set of aspects or features from imaging data acquired from a plurality of high-throughput data acquisition tools, build an ontological classification profile based on features extracted from massive quantities of raw data, and apply the classification profile within or across data sets. Since a single instance of such analysis may use the functions or capabilities of a plurality of data acquisition tools (which can include one or more data processing system such as one or more computational tools), the systems, methods, and devices described herein may accomplish analysis and classification of a given data set by routing data to various modules, subsystems, or additional data acquisition tools.

The systems described herein may be used to analyze and/or classify data originating from image acquisition systems such as systems comprising a camera or a microscope. For example, the systems, methods, and devices described herein are well-suited for analysis of imaging data produced during growth and toxicity assays involving either prokaryotic or eukaryotic cells, including microbes (e.g., yeasts such as *Saccharomyces cerevisae*, bacteria such as *Escherichia coli*, or mutant variants thereof), mammalian cells, and other primary cells and cell lines (e.g., cell lines with or without artificially modified genetic material). For example, the systems, methods, and devices can be used to analyze data collected from cellular assays (e.g., colony growth or cellular toxicity assays involving yeast or bacteria) performed on liquid media substrates (e.g., liquid broth media such as YPD broth, wherein cellular specimens may be pooled) or solid media substrates (e.g., solid agar substrates). In some embodiments, data sets that can be analyzed or classified using the systems, methods, and devices described herein can be derived from a variety of assays and experiments, including antibiotic, biomarker, and drug screening assays, cellular growth assays, bio-prospecting assays (e.g., experiments pertaining to development of cellular strains for regenerative medicine, industrial biofuel production, agricultural microbial products and crop modifications, or environmental rehabilitation), molecular expression functional activity assays (colorimetric or fluorescent reporter molecules associated with enzyme, protein, RNA or metabolite production, such as antibody-linked reporters, genetically expressed reporters, or cell-permeable or non-cell-permeable dyes), morphologic behavior (structural assembly variation) and experiments pertaining to the identification and/or characterization of pathogenic or virulent cell types. Moreover, the systems, methods, and devices allow for analysis (e.g., feature extraction, classification, and/or comparison) of experimental data for individual experimental groups (e.g., a certain strain of yeast) across as many as 50, 100, 200, 500, 1000, 5000, 10000, or even 100000 experiments (e.g., analysis stacking), which may comprise an extremely large number of experimental conditions in aggregate. In some embodiments, these analytical modalities can be repeated for each experimental group of a plurality of experimental groups, wherein the plurality of experimental groups can comprise 50, 100, 150, 200, 250, 500, 1000, 2500, 5000, 7500, or 10000 different specimens (e.g., cells comprising a different genetic modification or background).

The use of systems, methods, and devices described herein allows for identification of phenotypic and functional characteristics from analysis of samples (e.g., individual genetic variants) on a scale necessary for pharmacogenomic screening, quantitative trait mapping, synthetic biology, and systems biology approaches in both industrial and academic settings. For example, one or more complex trait (e.g., wherein multiple genes contribute to single phenotype) and/or one or more pleiotropic trait (e.g., wherein a single gene contributes to multiple phenotypes) can be identified or recognized in a specimen using the systems, methods, and devices described herein. In some embodiments, one or more correlation may be established between a set of experimental conditions (e.g., genetic strain of a cellular specimen or treatment conditions) and a set of one or more complex trait and/or one or more pleiotropic trait in a specimen. In some embodiments, advantages conferred by the capabilities of the systems and methods described herein (e.g., as a result of capacity for increased scale of experimental interrogation and data collection, highly controlled repeatability, high sampling rate, prolonged duration of data set collection, efficient data analysis, and/or statistical robustness resulting from cumulative accrual of analytical assets). These advantages allow for both analytical and predictive approaches to applications such as understanding associations between genotype and phenotype, mapping complex molecular pathways, understanding structural, chemical, and electrical cell-to-cell interactions in three-dimensional environments, and determining temporal expression patterns of RNA or proteins.

While described herein primarily in terms of analysis and classification of image-based data acquired from cell-based assays, it is contemplated that the systems, methods, and devices described herein can be used to analyze and classify virtually any data set. For example, the systems and methods described herein can be useful in the analysis (e.g., classification) of data sets produced or collected by non-imaging modalities (e.g., data from an electrochemical detection assay received from an instrument or 3rd party tool). In some embodiments, analysis of non-image-based data (e.g., data or metadata received from an instrument, user, or 3rd party tool) may be used to modify one or more data set used by the system for analysis (e.g., a feature data set, a training data set, or classification data set).

FIG. 1 shows an embodiment of system 100, which can be useful in high-throughput phenotypic analysis of cellular assay data. System 100 can include a plurality of components in communication with one another, for example, via a local network connection or a telecommunication network connection (e.g., a telecommunication network in communication with platform system 101). A component of system 100 can be a physical component (e.g., a user terminal 102 such as a computer or workstation, a data acquisition system 106, 108, a computational tool 104, a router, a server, a processor, a controller, a data storage medium, or an automated device) or a virtual component (e.g., a software module 110, 120, 130, 140, 150 or software subsystem thereof). In some embodiments, one or more first component of system 100 can control one or more second component of system 100, for example, through the transmission of instructions from the one or more first component to the one or more second component.

System 100 can comprise one or more user terminal 102, and one or more data acquisition systems 106, 108 (e.g., instrument 106, 108) or one or more computational tool 104. User terminal 102 can comprise a computer, a mobile device, or a workstation. User terminal 102 can be connected to system 100 by connection 103, which can be a wireless connection or a physical connection (e.g., a wired connection which may or may not involve wireless components, such as a wireless router). A data acquisition system can comprise an instrument 106, 108 (e.g., a microscope, an experimental condition management system such as a fluidics system or culture plate management system, an environment control system such as an incubator, an imaging system comprising a detector such as a camera and/or a source of radiation such as a laser or other illumination device).

One or more user terminal 102 may be connected to one or more additional user interface and/or to one or more data acquisition system by platform system 101. One or more user interface terminal 102 may also be connected to one or more additional user interface and/or to one or more data acquisition system via a local network connection.

System 100 can include integrated modules for division and/or completion of individual tasks. System 100 can comprise a platform system 101 that can include, for example, an application module 110, an instrument gateway module 120, an analysis engine module 130, an interface module 140, and a storage module 150. A subsystem or module of either system 100 or platform system 101 may be connected to one or more subsystem or module of either system 100 or platform system 101, for example, to facilitate efficient analysis of stored or acquired experimental data. Application module 110 can provide services and tools related to the user interface for the system 100 for integrated high-throughput phenotypic analysis of cellular assay data. Application module 110 can receive one or more client request from the user (e.g., via connection 103) and route or transmit the client request to one or more module or subsystem of system 100. In some embodiments, the application module 110 can communicate information, such as settings, experimental results, analyzed data, and instructions for carrying out the high-throughput automated phenotypic analysis of the cellular assay data, between a system client (e.g., a user) and one or more module or subsystem of system 100. For example, a system client may communicate an experiment design (e.g., input or transmit a client request) to experiment design subsystem 112 of application module 110 via a connection 103 using user terminal 102. After being selected or defined by a client, an experimental design can be communicated to an instrument for execution (e.g., via instrument gateway module 120) or to a subsystem comprising memory (e.g., storage module 150) for future use.

Experiment design subsystem 112 can be configured to provide tools to a client useful in designing an assay (e.g., for execution by one or more data acquisition system 106, 108). For instance, experiment design subsystem 112 can allow a client to define one or more aspect (e.g., one or more configuration parameter) of an experiment design, including one or more configuration parameter for one or more data acquisition system 108 (e.g., for communication to instrument gateway module 120), one or more analysis method (e.g., for communication to analysis engine module 130), one or more computational tool 104, or one or more additional data acquisition tool 106 (e.g., for communication to interface module 140).

A configuration parameter can be an experimental variable. In some embodiments, a configuration parameter can be an environmental condition or parameter, a treatment condition or parameter, a time parameter, a calibration parameter, an imaging method or condition, an image or data analysis method or algorithm, a detectable metric or feature, or a classification profile or method. For instance, a configuration parameter can be a number of experimental or control groups or replicates for an experiment, an experimental time point or endpoint, a statistical method, a threshold value (e.g., for image analysis, for statistical stringency, or for maintenance of environmental conditions), or a definition of one or more instruments to be used to carry out an experiment.

In some embodiments, a configuration parameter of an experiment design can comprise one or more custom (e.g., user-defined) configuration parameter, one or more pre-defined (e.g., stored) configuration parameter, or a combination of one or more custom configuration parameter and one or more pre-defined configuration parameter. A pre-defined configuration parameter may be defined by a configuration or software parameter of a data acquisition system, a configuration or parameter of stored data (e.g., a stored experimental design or classification profile). In some embodiments, a custom configuration parameter may be defined by, limited by, or informed by an aspect of a module or component with which the application module is in communication. For example, a custom configuration parameter may be defined by or limited by the capabilities or preset parameters of an instrument or additional data acquisition tool selected for an experiment or by the set of configuration parameters of a selected stored experiment design (e.g., as communicated to application module 110 by storage module 150), and it may be informed by actual environmental conditions detected in or around data acquisition system 106, 108 (e.g., as communicated to application module 110 by instrument gateway module 120).

Data visualization subsystem 114 can be configured to provide a user interface for viewing, interpreting, and visualizing the data and analysis results for an assay. Data visualization subsystem 114 can be used to present raw, partially processed, or fully processed data. Data presented to a client of system 100 can be qualitative or quantitative. Data visualization subsystem 114 can present data according to preset visualization profiles and functions or user-defined visualization preferences, which, in some embodiments, can each be selected prior to, during, or after the collection or presentation of experimental or analyzed data (e.g., by user input via connection 103). Preset visualization profiles and functions and user-defined visualization preferences can be stored in storage module 150. The format of data presented via data visualization subsystem 114 can comprise graphs, tables, charts, image stacks, three-dimensional renderings, movies (e.g., movie data captured as such by a data acquisition system or static images stitched together after collection), or a combination thereof.

In some embodiments, data can be presented via data visualization subsystem 114 in real-time or near real-time. For example, data produced, collected, or analyzed using a remote or local data acquisition system or using an additional data acquisition tool 106 or computational tool 104 can be transmitted to data visualization subsystem 114 (e.g., via one or more module or subsystem of system 100) for immediate display. In some embodiments, data presented by data visualization subsystem 114 can be refreshed or updated without lag (e.g., in real-time) or with minimal lag (e.g., near real-time presentation, which can, in some embodiments, result from real-time data analysis performed by a module or subsystem of system 100). In some embodiments, data can be presented in batch mode, which can comprise delaying the display of all or a portion of the collected or processed data (e.g., so that all or a portion of the data may be displayed at the same time). Batch mode presentation or analysis of data may be advantageous or necessary, for example, because it can allow for batch mode processing and can allow for low-cost processing and/or data storage availability.

Data presented via data visualization subsystem 114 can comprise experimental data (e.g., images captured during an experiment or partially processed images), analyzed experimental data (e.g., data resulting from quantitative or qualitative analysis of experimental data such as image data, feature data, graphs comprising raw data, processed data, or metadata), classification data (e.g., one or more classification profiles, one or more feature data set, and/or one or more experimental data set), classification results (e.g., as determined from classification of an experimental group or specimen), experimental condition data (e.g., measured environmental data such as temperature, humidity, barometric pressure, atmospheric gas composition, and camera or lighting settings), stored data, or metadata (such as time-based metrics like treatment or exposure durations and image capture intervals).

Data visualization subsystem 114 can be used to present imaging data recorded during an experiment. Imaging data can comprise individual sample or whole-plate images, time-lapse image series (e.g., images from an experiment edited together and presented with movie playback or slider bar controls). Imaging data can be raw, partially processed, or fully processed.

Raw or analyzed data can be passed to data visualization subsystem 114 from another module or subsystem of system 100. For example, raw data can be transmitted from instrument gateway module 120 to data visualization subsystem

114. In some embodiments, raw data can be passed from a subsystem of instrumentation gateway module 120, such as image ingest subsystem 122 or instrument monitoring subsystem 126. In some embodiments, data can be transmitted to data visualization subsystem 114 from a subsystem of analysis engine module 130 (e.g., image processing subsystem 132, feature extraction subsystem 134, or classification subsystem 136). Raw or analyzed data can also be passed to data visualization subsystem 114 from storage module 150, and subsystems thereof. Data can be transmitted to the data visualization subsystem 114 from interface module 140 and subsystems thereof (e.g., after receipt from an additional data acquisition system 106). In some embodiments, data from experiment monitoring subsystem 116 of application module 110 can be passed to data visualization subsystem 114.

Application module 110 can comprise experiment monitoring subsystem 116, which can be configured to provide status monitoring of the one or more data acquisition system 106, 108 or computational tool 104, during operation of the one or more data acquisition system (e.g., during data acquisition of a given assay). Experiment monitoring subsystem 116 can produce or comprise a means for producing a user interface for display of data or parameters relating to an experiment (e.g., a cellular assay).

For example, the status of a data acquisition system (e.g., an instrument 108 or an additional data acquisition tool 106) or computational tool 104 may be passed to experiment monitoring subsystem 116 by instrument gateway module or a subsystem thereof. For example, a sensor of a data acquisition system (e.g., an instrument 108) can detect or measure one or more aspect of an experiment or of data acquisition system 106, 108 (e.g., one or more environmental condition, experimental parameter, time-based condition, analysis parameter, device status code, error code) and transmit the detected or measured data to experiment monitoring subsystem 116. In some embodiments, experiment monitoring subsystem 116 can comprise a memory or storage cache into which data can be stored (e.g., a short-term storage cache or buffer for collection of experimental data to be displayed).

In some embodiments, data can be presented via experiment monitoring subsystem 116 in real-time or near real-time. For example, data collected or analyzed using a remote or local data acquisition system or using an additional data acquisition tool 106 or computational tool 104 can be transmitted to experiment monitoring subsystem 116 (e.g., via one or more module or subsystem of system 100) for immediate display. In some embodiments, data presented by experiment monitoring subsystem 116 can be refreshed or updated without lag (e.g., in real-time) or with minimal lag (e.g., near real-time presentation, which can, in some embodiments, result from real-time data analysis performed by a module or subsystem of system 100). Experiment monitoring subsystem 116 can also be operated in batch mode, which can comprise delaying the presentation of all or a portion of the collected or processed data (e.g., so that all or a portion of the data may be presented at the same time).

In some embodiments, experiment monitoring subsystem 116 may present a user with unrequested information and may, optionally, prompt the user for input (e.g., a client request). For example, if one or more status code or error message is received from one or more data acquisition system 106, 108 or computational tool 104, experiment monitoring subsystem 116 may present the one or more status code or error message to the user. In some embodiments, experiment monitoring subsystem 116 may present the user with a prompt to input preferences or commands (e.g., a client request) in response to the one or more status code or error message (e.g., to be transmitted to the one or more data acquisition system 106, 108 or computational tool 104). In some embodiments, a client request inputted by a user in response to a status code or error message may cause a modification or rectification of a status (e.g., an operational error of a data acquisition system 106, 108 or computational tool 104 or an experimental parameter).

Instrumentation gateway module 120 can provide an interface to one or more instrument 108 and a means for communicating with the one or more instrument 108. Instrument gateway module 120 can transmit data (e.g., instructions such as client requests) from one or more client (e.g., user terminal 102, computational tool 104, or data acquisition system 106, 108) to one or more instrument 108. Data (e.g., experimental data) transmitted from instrument gateway module 120 to a computational tool 104, or data acquisition system 106, 108 can comprise experiment design information, setup or configuration instructions, status requests, instructions to initiate or terminate an operation (e.g., experiment initiation or termination instructions), or data originating from other modules, subsystems, instruments, or clients (e.g., an additional data acquisition tool 106 or computational tool 104). Instrument gateway module 120 may also receive any type of data from an instrument, module, or subsystem of system 100.

Instrument gateway module 120 and associated instruments and data acquisition computational tools can be configured to acquire very large experimental data sets. For example, testing of this system has shown that a high rate of sampling for collection of experimental data can yield unexpected levels of insight into the function and/or phenotype of a specimen (e.g., as a result of more precise dissection of temporal events and/or improved statistical resolution of subtle changes in quantifiable metrics); however, sampling at such a high rate can produce quantities of data that other systems and methods are not able to receive, analyze, classify, and/or store efficiently, if at all. In some embodiments, a high rate of sampling comprises sampling at less than the doubling rate of a cellular specimen, less than half the doubling rate of a cellular specimen, less than one third the doubling rate of a cellular specimen, less than one quarter the doubling rate of a cellular specimen, or less than one eight the doubling rate of a cellular specimen (e.g., when doubling rate is measured in a log phase of cellular growth). In some embodiments, the doubling rate of a microbial species (e.g., bacteria, fungi, like yeast) can range from 10 minutes to 45 minutes, from 15 minutes to 30 minutes, from 20 minutes to 25 minutes, from 45 minutes to 60 minutes, from 60 minutes to 90 minutes, from 90 minutes to 180 minutes, from 90 minutes to 140 minutes, or from 105 minutes to 120 minutes.

In some embodiments, instrument gateway module 120 may automatically transmit (e.g., without requiring user input) data received from another module or client to one or more data acquisition system 106, 108 or computational tool 104. For example, during execution of an experimental design requiring the coordinated function of two or more instruments, modules, and/or additional data acquisition tools, instrument gateway module 120 may send data received from a first instrument or module of system 100 to a second instrument or module of system 100 automatically. In some embodiments, data acquired from instrumentation gateway module 120 can comprise an image ingest subsystem 122. Image ingest subsystem 122 may be configured to accept data (e.g., experimental data) captured by one or more data acquisition system 106, 108 during operation (e.g., during execution of an assay of an experiment). In some embodiments, data received by image ingest subsystem 122 may include, but is not limited to, images of plated cellular samples, environmental data (e.g., parameters such as temperature, percent gas composition, and humidity), instrument settings (such as shutter speed, focal point, and duration of exposure) and sample traceability data (such as barcoding, QR codes, or RFID), and sample plate calibration information (e.g., data relating to one or more of a dimension, feature, hue, saturation, contrast, intensity, or other colorimetry parameters of a sample). Image data passed to image ingest subsystem 122 can be individual static images, grouped static images (e.g., image stacks), or movie files.

Instrumentation gateway module 120 can comprise instrument setup subsystem 124, which can be configured to receive experimental data comprising one or more configuration parameter. Instrument setup system 124 can be configured to transmit a client request to data acquisition system 106, 108 or computational tool 104 and/or to receive one or more configuration parameter for an assay (e.g., one or more parameter of an experiment design) from data acquisition system 106, 108. In some embodiments, a configuration parameter may be a capture interval, a plate configuration, a number of samples (e.g. a number culture plates or biological samples on a culture plate), an identification number (e.g., of an experiment or portion of an experiment such as a plate or region of a plate), an imaging parameter (e.g., a setting related to a filter or image filtering method, a setting related to an illumination source, a setting related to signal detection such as selection of a detection method or specification of a gain level, intensity threshold, or contrast threshold), a start time, or a duration (e.g., a duration of an experiment or capture event such as shutter speed of an imaging event). In some embodiments, data may be received by image setup subsystem 124 from experiment design subsystem 112 and transmitted to instrument 108.

Instrumentation gateway module 120 can also comprise instrument monitoring subsystem 126. Instrument monitoring subsystem 126 can be configured to receive the instrument status data from one or more instrument 108. Instrument status data, which can comprise experimental data, can be transmitted from instrument monitoring subsystem 126 to another module or subsystem of system 100. For example, instrument monitoring subsystem 126 may pass instrument status data from one or more instrument 108 to experiment monitoring subsystem 116. In some embodiments, data transmitted or received by instrument monitoring subsystem 126 can comprise instrument user/operator logs, experiment runtime logs, error logs, temporal environmental condition data (e.g., relating to internal conditions of one or more instrument 108), service history, hardware configuration information, and software configuration information.

Analysis engine module 130 can be configured to perform analysis of experimental data produced, stored, or received by one or more component of system 100. For example, analysis engine module can be used to automatically perform phenotypic classification of cellular samples of an assay. In some embodiments, analysis engine module or a subsystem thereof may use data created or received by system 100 (e.g., experimental data such as raw image data as well as or instead of feature data extracted from experimental data) to build a new classification profile or to revise an existing classification profile. Analysis engine module 130 or a subsystem thereof may also apply a classification profile (e.g., a stored classification profile or a newly created classification profile) to a data set (e.g., in order to classify one or more experimental group, such as one or more specimen of an experiment). Data useful for creation or revision of a classification profile can be raw data, partially processed data, or fully processed data. In some embodiments data used by analysis engine module 130 can be extracted feature data and can comprise a feature data set.

Analysis engine module 130 can comprise image processing subsystem 132, which can be configured to preprocess images in preparation for feature extraction. Image processing subsystem 132 can apply one or more image processing method to an input image stream received, for example, from one or more of the instrument 106, 108. An image processing method can be defined by and passed to analysis engine module 130 from storage module 150, a computational tool 104, an additional data acquisition tool 106, or a user input (e.g., via a user terminal 102).

Image processing subsystem 132 can be configured to identify aspects of an image (e.g., image features) and can, in some embodiments, apply one or more modification to one or more image of the input image stream, such as filtering, thresholding, gray-scaling, Gaussian blur. In this way, partial processing of one or more image of an image stream collected by an instrument 106, 108 can be accomplished by image processing subsystem 132. Whether preprocessing is performed by image processing subsystem 132 and the combination and, if so, the degree to which processing methods are applied by image processing subsystem 132 can comprise a client request (e.g., comprising an experimental design) passed to analysis engine module 130 from application module 110 or an aspect of an experimental design stored in storage module 150 and selected by a user or used as a default method for a certain experimental design. Image processing subsystem 132 can transmit one or more raw or partially processed image of an image stream to feature extraction subsystem 134. In some embodiments, a partially processed image can comprise data in a positive file format, such as TIFF or JPEG formatting.

In some embodiments, image processing subsystem 132 can receive and process a raw image sensor file (e.g., from an instrument 106, 108 or from storage module 150) or an image previously converted to a positive file format (e.g., by instrument 106, 108, or by another module, subsystem, or component of system 100). For example, image processing subsystem 132 can convert a raw image sensor file (e.g., raw image data) to a positive file format such as TIFF or JPEG before passing the data to another subsystem of the analysis engine module, such as feature extraction subsystem 134.

Feature extraction subsystem 134 can be configured to receive and process the data output of the image processing subsystem 132. For example, feature extraction subsystem 134 can receive one or more image of an image stream from image processing subsystem 132 and can be used to extract one or more feature from the one or more image. In some embodiments, feature extraction subsystem 134 can be used to measure image features of a cellular sample. Feature data that can be extracted from collected and/or processed data (e.g., experimental data, such as image data) can comprise one or more quantitative or qualitative aspect of an image. In some embodiments, a feature data set may comprise both one or more quantitative aspect of an image and one or more qualitative aspect of an image.

Feature data (e.g., image feature data) extracted by feature extraction subsystem 134 may include, but are not limited to, object detection, object counting, circularity, statistical measurements of intensity and color channel (e.g., absolute intensity, hue, and/or saturation measurement or measurement of spatial changes in intensity, hue, and/or saturation), edge detection, segmentation and segment counting, and/or dimensional measurement (e.g., length, thickness, area or diameter measurement). In some cases, feature data may be extracted based whether the data meets or exceeds one or more threshold value. In some embodiments, feature data may comprise one or more feature determined or calculated from one or more other feature data set (e.g., a relative measurement). For example, an object's height may be calculated from one or more measurement of intensity and/or data comprising a position of the focal plane of the image. In some embodiments, feature extraction subsystem 134 may comprise a method for identifying or quantifying a centroid of a cell or group of cells (e.g., a colony of cells, which can comprise a plurality of cells that are physically associated or unassociated with one another), relative position of an object or group of objects (e.g., with respect to the same object in a time course or with respect to a second object, such as a cell, or group of objects, such as a colony of cells, at a given time point or over a time course), a method of using regions of interest (ROIs) or masked image data to determine a boundary of an object (e.g., for determining differences in cell or colony position or size) or group of cells (e.g., a colony of cells), a method of determining the one or more dimension or quality of a portion of an image (e.g., a determination of the length and/or thickness of a cellular filament or portion thereof), or a method of texture segmentation (e.g., a method of determining cellular edge ruffling, halo features of a cell or colony, or ridged features of a cell or colony).

Feature data can also comprise data determined or calculated by comparing a plurality of data sets. In some embodiments, feature data can be calculated or otherwise determined by comparing two or more individual frames of a video and/or two or more images in a temporal sequence of images, such as a time lapse image set. For example, colony growth rate can be determined by measuring and comparing a colony diameter in two or more images of an experimental data set.

Feature extraction subsystem 134 can transmit processed (e.g., partially processed or fully processed) image data and/or extracted feature data from images of an image stream to the classification subsystem 136. In some embodiments, feature extraction subsystem 134 can send data, which may include one or more extracted feature of one or more image of the image stream, to the classification subsystem 136 without sending the images themselves.

Analysis engine module 130 can comprise classification subsystem 136 for classification of one or more data set and/or one or more experimental group (e.g., one or more specimen of an experiment) based on raw, partially processed, and/or fully processed data (e.g., raw image files, extracted features, and/or data produced by additional data acquisition tools). Classification of one or more data set and/or one or more experimental group (e.g., one or more specimen, such as a cell type) can involve assigning a functional or phenotypic label or categorization to the data set or experimental group or categorizing the data set or experimental group based on a functional or phenotypic trait of the data set or experimental group (e.g., as determined by a comparison of the data set or a data set related to the experimental group to one or more additional data set, such as a data set related to a different experimental group). Classification of one or more data set and/or one or more experimental group can comprise applying a classification profile to a data set of an experiment or the compiled or aggregated data from a plurality of data sets or experiments.

In some embodiments, classification subsystem 136 can comprise grouping data sets or experimental groups by a functional or phenotypic parameter (e.g., as determined from classification of experimental data). In some embodiments, classification subsystem 136 can comprise a memory or storage cache into which data can be stored (e.g., a short-term storage cache or buffer for collection of experimental data to be displayed).

A classification profile can be built (e.g., created, compiled, revised, or modified) by comparing two or more data sets in which a relationship between at least one aspect of each data set and at least one functional or phenotypic aspect of the data set is known (e.g., in order to better define the parameters governing the relationship between the at least one aspect of the data set and the at least one functional or phenotypic aspect of the data set). In some embodiments, a classification profile can be built by analysis engine module 130 or a subsystem thereof (e.g., classification subsystem 136) using a machine learning algorithm. In some embodiments, a classification profile can be built using a labeled training data set (e.g., supervised classification), and, in some embodiments, a classification profile can be built without using a labeled training data set (e.g., unsupervised classification). A labeled training data set can comprise a sample data set (e.g., comprising experimental data, calculated data, and/or data from another source such as one or more scientific literature source) that bears an indication of a feature, function, phenotype, classification, or other categorization represented by at least a portion of the labeled training data set. In some embodiments, a classification profile can be an interrogation filter. In some embodiments, a classification profile can be inputted by a client of system 100 (e.g., via application module 110 or interface module 140) and may be stored in a module or subsystem of system 100 (e.g., storage module 150 or classification subsystem 136).

Classification subsystem 136 may apply a method of classification to a data set (e.g., a data set comprising one or more feature data set), depending, for example, on the configuration of the assay from which the data being analyzed is derived. A method of classification can comprise a supervised method of classification or an unsupervised method of classification. A method of classification (e.g., a method of applying a classification profile to a data set) can comprise dimensionality reduction, one or more Monte Carlo-based technique (e.g., Monte Carlo random sampling, Markov chain Monte Carlo, or Monte Carlo feature selection), clustering and anomaly detection, regression modeling, principal component analysis, linear discriminant analysis, binary, multi-class and linear classification based on labeled training data.

In some embodiments, a validation technique can be used to validate a classification result. For example, cross-validation using standard measures such as accuracy and precision may be employed for validation of a classification result.

In some embodiments, classification subsystem 136 may use one or more aspect of a data set (e.g., one or more raw image or portion thereof and/or one or more extracted feature such as a distance, a diameter, or an image contrast and complexity assessment) to determine one or more phenotypic or functional characteristic of the data set or of one or more parameter producing the data set (e.g., an experimental group, such as a cell type). In some embodiments, one or more relationship between an aspect of a data set and a phenotypic or functional characteristic (e.g., as determined by classification subsystem 136) can be stored in a memory-containing module of system 100 (e.g., a short-term storage cache or a long-term data subsystem of one or more of storage module 150, analysis engine module 130, or classification subsystem 136). In some embodiments, one or more relationship between an aspect of a data set and a phenotypic or functional characteristic can be compiled into a classification profile, which can be stored in a module or subsystem of system 100 comprising memory.

In some embodiments, classification subsystem 136 may perform predictive classification of data as it is received by a module or subsystem of system 100. In some embodiments, predictive classification can be performed in real-time or near real-time as data is received by classification subsystem 136. Predictive classification can comprise the use of machine learning methods or algorithms.

Classification subsystem 136 can be configured to receive data from image processing subsystem 132, feature extraction subsystem 134, storage module 150, or a combination thereof, in conjunction with other data points gathered or used by instruments 106, 108, application module 110, interface module 140, or instrumentation gateway module 120. In some embodiments, data used by classification subsystem 136 can comprise metadata, experiment design information, or configuration parameters.

Interface module 140, which may be a software-as-a-service (SaaS) API Layer, can be configured to provide a web services interface (e.g., a REST API) and/or one or more software development kit for one or more software application or instrument to access, control, and interact with the rest of the system 100. For example, may comprise a portal for transmission of a client request (e.g., an experiment design or portion thereof or instructions to execute an experiment design) to a remote additional data acquisition tool. In some embodiments, interface module 140 can comprise a software development kit useful in creating software to be used in interfacing with a computational tool 104 or an additional data acquisition tool 106 with system 100.

Interface module 140 can comprise image ingest API subsystem 142, which can be configured to provide for the integration of instrumentation or tools to access the image ingest subsystem 122. In some embodiments, image ingest API subsystem 142 can receive data (e.g., experimental data such as image data, extracted feature data, metadata, or data related to a classification profile or protocol) into system 100. For example, rules or routines comprising image ingest API subsystem 142 may be used in the receiving of imaging data from an additional data acquisition tool 106 (e.g., an instrument 106) and subsequently transmitting the data to image ingest subsystem 122 (e.g., for further analysis or storage in one or more module or subsystem of system 100). In some embodiments, software or firmware may be received by platform system 101 from one or more additional data acquisition tool 106 or computational tool 104 via image ingest API subsystem 142.

Interface module 140 can comprise analysis API subsystem 144, which can be configured to provide a means of integrating one or more computational tool 104 and/or one or more additional data acquisition tool 106 with analysis module 130 (e.g., feature extraction subsystem 134 and/or classification subsystem 136). In some embodiments, analysis API subsystem 144 can transmit data received from one or more computational tool 104 or additional data acquisition tool 106 (e.g., via image ingest API subsystem 142) to another module or subsystem of system 100. For example, analysis API subsystem 144 can communicate data created or processed by computational tool 104 or by an additional data acquisition tool 106 and received by image ingest API subsystem 142 to image processing subsystem 132, feature extraction subsystem 134, or classification subsystem 136.

Interface module 140 can also comprise storage API subsystem 146, which can be configured to communicate data from storage module 150 to one or more computational tool 104 or additional data acquisition tool 106, or vice versa. For example, data produced by a computational tool 104 or an additional data acquisition tool 106 may be downloaded to system 100 via storage API subsystem 146. In some embodiments, stored data may be exported to one or more computational tool 104 or one or more additional data acquisition tool 106 via storage API subsystem 146. For example, experiment design or experiment metadata may be received from experiment definition subsystem 152 or experiment metadata subsystem 154, respectively, and transmitted to one or more computational tool 104 or one or more additional data acquisition tool 106 (e.g., in order for an experiment to be carried out using one or more additional data acquisition tool). In some embodiments, data used by one or more computational tool 104 or one or more additional data acquisition tool 106 may be transmitted from storage module 150 (or a subsystem thereof, such as long-term image store subsystem 158) via storage API subsystem 146.

In some embodiments, a plurality of subsystems of interface module 140 may be used to communicate data between system 100 and one or more computational tool 104 or one or more additional data acquisition tool 106 for the purpose of data analysis and/or classification. For example, analysis API subsystem 144 and/or storage API subsystem 146 may be used to access image processing methods or algorithm libraries, visualization tools, or sample metadata for data classification.

In some embodiments, a plurality of subsystems of interface module 140 may be used to communicate data (e.g., download data to system 100 or export data to one or more computational tool 104 or one or more additional data acquisition tool 106) for the purpose of allowing a computational tool 104 or an additional data acquisition tool 106 to access the data, methods, algorithms, functions, or protocols of one or more module or subsystem of system 100. For example, an additional data acquisition tool 106 may transmit image data to system 100 via image ingest API subsystem 142 to be transmitted to analysis engine module 130 by analysis API subsystem 144 for analysis and subsequent export through interface module 140 or data storage in storage module 150.

Storage module 150 can comprise subsystems and methods for persistent storage and data management. Storage module 150 and subsystems thereof may receive data directly from or transmit data directly to any other module of system 100. Data stored in storage module 150 can comprise raw data, partially processed data, or fully processed data. For example, data stored in storage module 150 can include raw image data, extracted feature data, classification profile data, metadata, experiment design data, user profile or login data, interface data, or any other type of data described or implied herein.

Storage module 150 may include experiment definition subsystem 152, which can be configured to maintain the data associated with the execution of experimental assays and protocols. Experiment definition subsystem 152 may be used to store pre-defined methods and protocols for one or more assay, which can comprise an experiment design. Experiment definition subsystem 152 can also comprise custom (e.g., user defined) methods and protocols for one or more assay, which can also comprise an experimental design. Data stored in experiment definition subsystem 152 can be transmitted to instrument gateway module 120 or interface module 140 to define settings and/or to control or instruct one or more data acquisition system 106, 108 or computational tool 104 or communications therewith.

Storage module 150 can comprise experiment metadata subsystem 154, which can maintain intermediate and final data (e.g., partially or fully processed data) received from analysis module 130. Data stored in experiment metadata subsystem 154 can be transmitted to other modules and subsystems of system 100 in order to fulfill various functions. For example, data stored in experiment metadata subsystem 154 can be transmitted to classification subsystem 136 for data classification or to data visualization subsystem 114 for display. In some embodiments, data stored in experiment metadata subsystem 154 can be made available to one or more computational tool 104 or one or more additional data acquisition tool 106 via interface module 140 (e.g., for further data processing).

Image cache subsystem 156 of storage module 150 can comprise memory for maintaining data (e.g., image data) received from one or more data acquisition system 106, 108. In some embodiments, data maintained by image cache subsystem 156 can be transmitted to analysis module 130 for processing or classification. The image cache subsystem 156 may maintain the image data at a quality suitable for visualization by the application module 110. In some embodiments, data in image cache subsystem 156 can be maintained in more than one availability state, wherein an availability state can comprise image data having formatting or resolution conducive to instant, near-instant, or delayed processing, analysis, or visualization. In some embodiments, it is possible to more efficiently supply image data to one or more other module or subsystem of system 100 by maintaining image data in a plurality of availability states, depending on whether batch, near-real-time, or real-time processing, analysis, or visualization is used for a given client request or system function, which can, in turn, be determined at least in part by processing cost and/or storage availability.

Long term image store subsystem 158 of storage module 150 can be configured to maintain (e.g., store) image data acquired by data acquisition platform 106, 108 at a quality suitable for processing in an archived format (e.g., for long-term and/or low-cost storage).

Instrument cache subsystem 159 of storage module 150 can be configured to maintain data and information associated with a data acquisition system interface, such as an instrument configuration. Data received from instrument gateway module 120 or a subsystem thereof, which can include any processed or utilized by instrument setup subsystem 124 or instrument monitoring subsystem 126, can be stored in instrument cache subsystem 159. Data stored in storage module 150 or a subsystem thereof (e.g., instrument cache subsystem 159) can be transmitted by storage module 150 or the subsystem thereof to analysis engine module 130 or a subsystem thereof (e.g., image processing subsystem 132, feature extraction subsystem 134, or classification subsystem 136) for analysis, which can include classification.

Figure 2:
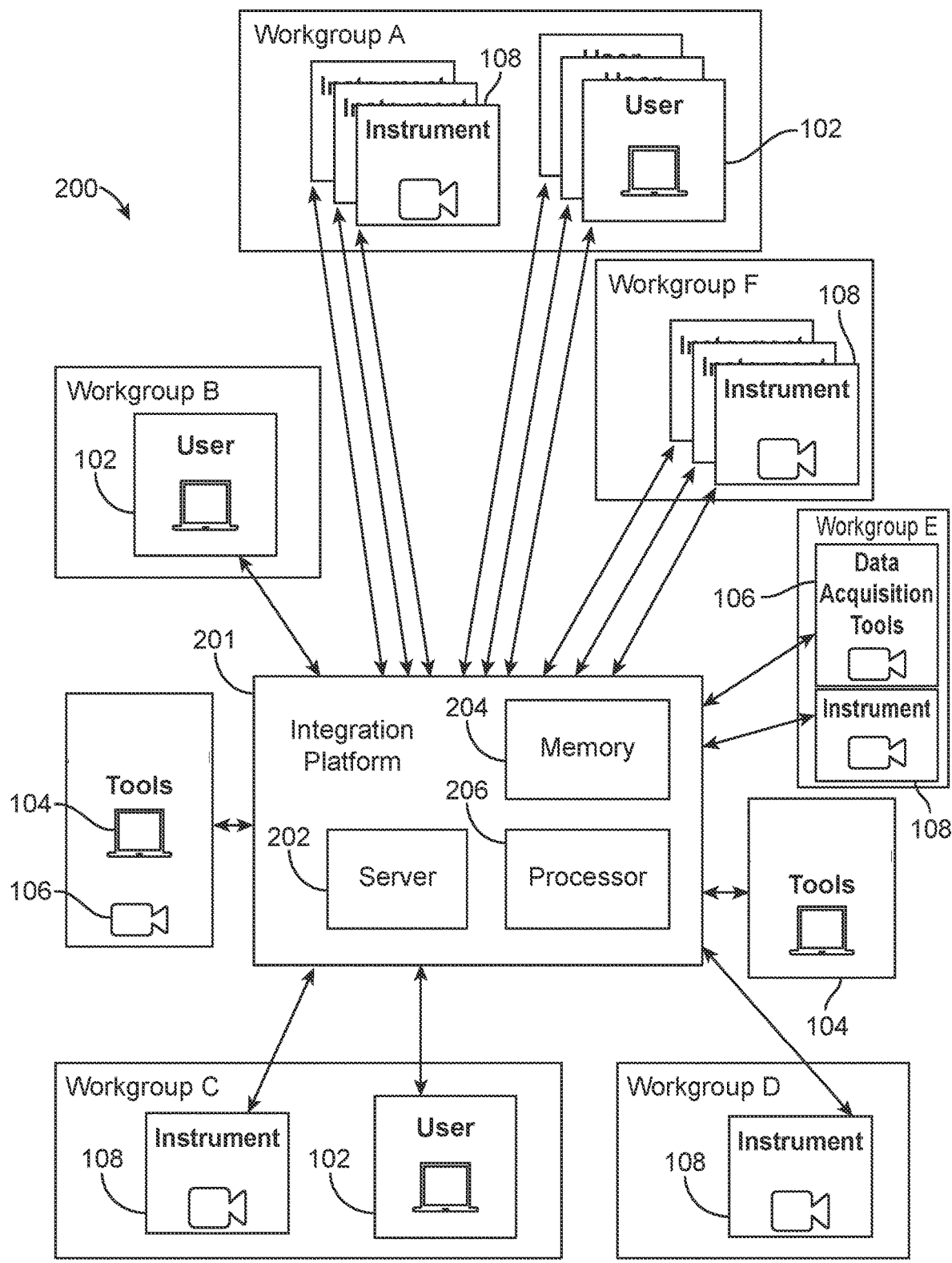
FIG. 2 shows a schematic diagram of a network for integrated high-throughput phenotypic analysis of cellular assay data in accordance with one or more embodiments disclosed herein.

Referring now to FIG. 2, system 200 can comprise a plurality of connections to a plurality of clients, where a client can comprise a device of system 200. Clients connected to integrated platform 201 can include individual user terminals, locally networked user terminals, individual instruments, locally networked instruments, additional data acquisition tools, and additional data processing tools such as computational tools. In some embodiments, a first and second instrument 106, 108 may be a first plurality of instruments and a second plurality of instruments, respectively. In some embodiments, system 200 can be an embodiment of system 100, and integrated platform 201 can be an embodiment of platform system 101. Integrated platform 201 (and, thus, platform system 101 as well) may comprise one or more server 202, one or more memory 204, and one or more processor 206 or controller. Modules, subsystems, or any function thereof may be coordinated, controlled, or executed by a controller or processor 206.

In some embodiments, a first portion of platform system 101 or integrated platform 201 (e.g., a first group comprising one or more module or subsystem as described herein) can be executed in a different computing environment than a second portion of platform system 101 or integrated platform 201 (e.g., a second group comprising one or more module or subsystem, as described herein). A computing environment for executing the functions of a first or second portion of platform system 101 or integrated platform 201 may comprise a client of system 100 or system 200. For example, a first portion of data used in the systems and methods described herein (e.g., experimental data, feature data, metadata, classification data, classification profile(s), classification results, image data, partially- or fully-processed data, or stored data) can reside permanently or temporarily in a different computing environment than a second portion of data used in the systems or methods described herein. In some embodiments, an encryption key may be employed by the computing environment or may be assigned to a portion of the data itself (e.g., cumulative cryptographic hashes).

A client (e.g., a user terminal 102, computational tool 104, or a data acquisition system 106, 108) may be connected directly to a module of integrated platform 201 (e.g., application module 110 or interface module 140), to one or more additional client (e.g., either locally or remotely). In some embodiments, a client can be connected to integrated platform 201 directly and to one or more additional client through the connection each client shares with integrated platform 201. In some embodiments, the access to one or more additional client granted to a first client can be determined by a module or subsystem of integrated platform 201. In some embodiments, such access can be granted to a first client for a limited period of time. In some embodiments, such access can be granted for compensation, such as a fee or mutual access granted to the one or more additional client. In some embodiments, a client can be assigned to a workgroup according to the customer and/or function with which the client is associated. A workgroup of system 200 can comprise one or more client. For example, a workgroup can comprise one or more user terminal 102 and/or one or more data acquisition system (e.g., one or more instrument and/or one or more additional data acquisition tool).

An instrument of system 100 can comprise any means of performing, measuring, detecting, or quantifying an aspect of an experiment or assay. For example, system 100 can comprise one or more instrument 106, 108, which can be a portion of a data acquisition system or an additional data acquisition tool. In some embodiments, instrument 106, 108 can comprise an image capture system, which can comprise one or more infrared light, visible light, fluorescent light or ultraviolet light detector (e.g., a photomultiplier tube or camera such as a digital camera capable of recording still images or video images), or a microscope. An instrument 106, 108 can also comprise a light source (e.g., an ultraviolet light source, an infrared light source, a laser light source, or a visible light source, which can comprise one or more configuration for enhancing contrast such as phase contrast, differential interference contrast, bright field, dark field, Hoffman modulation, or polarized light techniques) or a source of electrical or magnetic stimulation. In some embodiments, an instrument 106, 108 can comprise a mechanism for moving all or a portion of an image capture system, such as a motor, a two-dimensional or three-dimensional gantry, and/or a lens focusing system. An imaging system can be operated according to an imaging method, which can be, can depend upon, or can be limited by an experiment design.

In some embodiments, an imaging system of instrument 106, 108, such as a motorized camera system, can be automated. For example, the imaging method with which or order in which one or more sample (e.g., one or more plate comprising one or more specimen or colony of specimens) is assayed (e.g., imaged) can be automatically determined and/or controlled by one or more module or subsystem of system 100.

In some embodiments, instrument 106, 108 can comprise or be operated in a controlled environment. For example, instrument 106, 108 can comprise one or more of a temperature gauge (e.g., a thermometer), a humidification mechanism (e.g., a humidity pan, a humidification chamber, or a microhumidifier), a humidity sensor, a source of a gas (e.g., carbon dioxide, oxygen, nitrogen, methane or any combination thereof such as 5%, 10%, or 50% carbon dioxide in nitrogen, 5% or 10% carbon dioxide and 5% or 10% oxygen in nitrogen, or 10% oxygen in nitrogen), a gas concentration measurement system (e.g., a gas analyzer), or a heating source (e.g., an electrical heat source or water-insulated heating jacket). In some embodiments, instrument 106, 108 can comprise a spectroscope (e.g., ultraviolet-visible spectroscope, near-infrared spectroscope, X-ray chromatography equipment, atomic emission chromatography equipment, or a mass spectrometer such as LC-MS-MS), gas chromatography system, or a liquid chromatography system (such as high-performance liquid chromatography). In some embodiments, an instrument can comprise an environment at 0, 1, 2, 3, 4, 5, 6, 10, 15, 20, 21, 22, 23, 24, 25, 26, 27, 28, 29, 30, 31, 32, 33, 34, 35, 36, 37, 38, 39, 40, 45, 50, 55, 60, 65, 70, 71, 72, 75, 80, 85, 90, 95, or 100 degrees Celsius, and an experiment or assay, as described herein, can be performed at 0, 1, 2, 3, 4, 5, 6, 10, 15, 20, 21, 22, 23, 24, 25, 26, 27, 28, 29, 30, 31, 32, 33, 34, 35, 36, 37, 38, 39, 40, 45, 50, 55, 60, 65, 70, 71, 72, 75, 80, 85, 90, 95, or 100 degrees Celsius. For example, microbial growth assays can be performed at 37 degrees Celsius.

Instrument 106, 108 can also comprise a system for moving a sample before, during, or after an experiment. For example, instrument 106, 108 can comprise a sample handling system, which can comprise a culture plate management system and/or a fluidic system. A plate management system can comprise a plurality of culture plates or trays, which can each comprise 1, 2, 3, 4, 6, 12, 24, 48, 96, or 384 wells. In some embodiments, a plate management system can comprise a tray or plate stacker, a tray or plate selector, a tray or plate positioner, and/or a moveable microscope stage. In some embodiments, an instrument 106, 108 can be capable of capturing image data from at least one, at least two, at least three, at least four, at least five, at least six, at least seven, at least eight, at least nine, at least ten, at least eleven, or at least twelve single-well plates, 96-well plates or 384-well plates simultaneously.

In some embodiments, a sample management system of instrument 106, 108, such as a plate management system, can be automated. For example, the order in which one or more sample (e.g., one or more plate comprising one or more specimen or colony of specimens) is assayed (e.g., imaged) can be automatically determined and/or controlled by one or more module or subsystem of system 100.

In some embodiments, one or more aspect of instrument 106, 108 can be controlled by a module or subsystem of system 100. In some embodiments, one or more aspect of instrument 106, 108 can be operated automatically. One or more instrument 106, 108 of system 100 can be operated locally or remotely using instructions received from platform system 101. In some embodiments, a user can specify one or more measurement, statistical comparison, assay, experiment, or series of experiments to be performed using one or more specimen, and platform system 101 can automatically partition tasks, select equipment (e.g., one or more instrument 106, 108 based on instrument availability and/or capability) to perform the tasks, transmit instructions (e.g., an experiment design) to one or more instrument for obtaining the user-requested one or more measurement, comparison, assay, experiment, or series of experiments.

In some embodiments, system 100 can comprise one or more computational tool 104 or one or more additional data acquisition tool 106 with which system 100 communicates through an interface module. In some embodiments, an additional data acquisition tool can comprise an instrument 106 (e.g., additional data acquisition tool 106). In some embodiments, additional data acquisition tool can comprise a data processing tool (e.g., a computational tool 104 or computational platform). A data processing tool, which can, for example, comprise a computational tool 104, can comprise an analysis platform, such as a computational biology platform. In some embodiments, data transmitted to instrument 106 or data processing tool (e.g., computational tool 104) can undergo analysis (e.g., partially or fully processing or classification). Optionally, data analyzed by an instrument 106 or computational tool 104 can be received by platform system 101 (e.g., a subsystem of interface module 140) after analysis by the instrument or data processing tool. For example, one or more experimental data set, feature data set, and/or classification data set can be transmitted to a computational tool 104 where it can be analyzed and/or where computational tool 104 may build a classification profile, which can be received from computational tool 104 by interface module 140 or a subsystem thereof.

Figure 3:
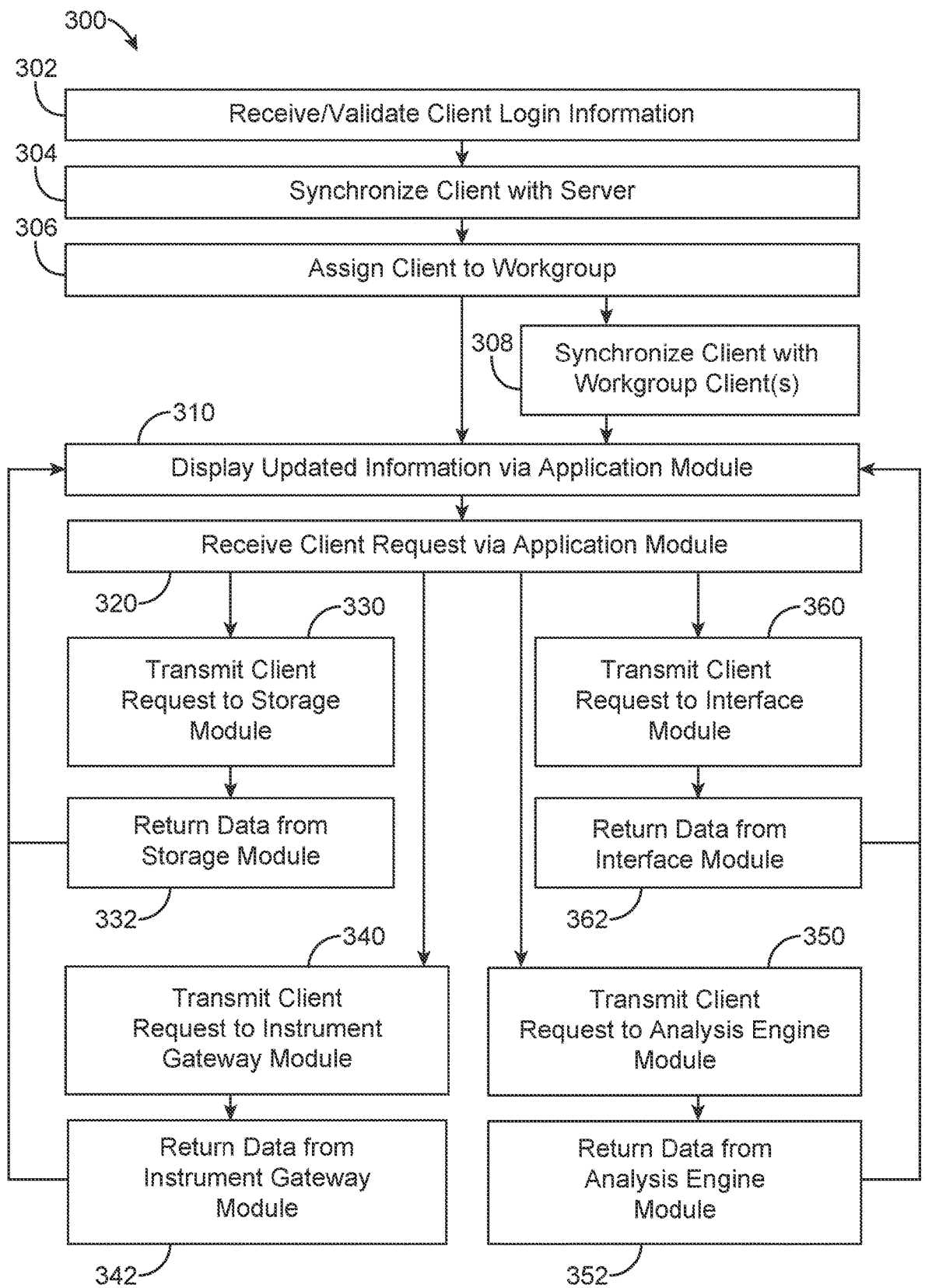
FIG. 3 shows a flow diagram of a method for coordinating integrated high-throughput acquisition and analysis of phenotypic cellular assay data in accordance with one or more embodiments disclosed herein.

Referring now to FIG. 3, process 300 represents an example of how a client (such as a user at a user terminal 102) may access all functionalities of system 100, as described herein. For instance, system 100 may receive and may validate login information from the client in a step 302. In some embodiments, a client can be a local area network account, which can be connected to one or more user terminal 102, one or more computational tool 104, and/or one or more data acquisition system 106. The client can be synchronized with a server of system 100 in a step 304. Synchronization of a client with a server of system 100 may comprise transmitting and/or receiving updated data, software, or firmware from the client to the platform system 101. In a step 306, the client may be assigned to a workgroup, which may or may not comprise one or more additional client. If the workgroup to which the client is associated also comprises one or more additional client, the client may be synchronized with all or a portion of the additional client(s) in the workgroup via system 100 in a step 308. In some embodiments, a workgroup can comprise one or more of a user terminal, a data acquisition system 108, a computational tool 104, and/or additional data acquisition system 106. A first client of a workgroup may be local or remote with respect to a second client of a workgroup and may or may not allow access to the second client of the workgroup (e.g., for the purpose of sharing data, experimental resources, or computational resources) and may or may not require compensation for said access.

After the client has been assigned to a workgroup and optionally synchronized with one or more additional client of the workgroup, data may be presented to the client in a step 310 reflecting update information pertaining to input options, ongoing or completed experiments, or stored data (e.g., via any of the subsystems of application module 110). At step 320, the client may input a client request to application module 110, which can be transmitted to instrument gateway module 120 (e.g., in a step 340), analysis module 130 (e.g., as in a step 350), interface module 140 (as in a step 360), and/or storage module 150 (e.g., as in a step 330). A client request can comprise one or more command (e.g., instructions to display at least a portion of a data set, instructions to operate a data acquisition system, instructions to create, edit, or delete data or to retrieve data from long-term or short-term storage, or instructions to perform one or more method of data analysis such as applying one or more classification profile to a data set) or one or more data set (e.g., wherein a data set can comprise experimental data, feature data, classification data, one or more classification profile, metadata, one or more aspect of an experimental design, or training set data). Commands (e.g., instructions) contained in the client request can be carried out by the modules and subsystems of system 100 automatically. For example, a client request may specify a plurality of assays be performed on a plurality of specimens and that one or more feature data set be extracted from the resulting experimental data set before one or more classification profiles is applied to the feature data set and that classification results be displayed in real-time, and platform system 101 can automatically task one or more data acquisition systems (e.g., via instrument gateway module 120 or via interface module 140, as in steps 340 and 360, respectively), request previously stored classification data be transmitted from storage module 150 to analysis engine module 130 (e.g., as in a step 330), and/or instruct analysis engine module 130 to execute one or more feature extraction or classification method on data received in analysis engine module 130 from instrument gateway module 120 or interface module 140 (e.g., as in a step 350). At step 332, 342, 352, and 362, data may be returned (e.g., received) from the instrumentation gateway module 120, analysis module 130, interface module 140, and/or storage module 150 for display via application module 110 (e.g., in batch mode display, in near-real-time display, or in real-time display). The system can accept additional client requests prior to, during, or after display of returned data in step 310.

In some cases, client requests may be stacked. For example, a plurality of client requests, which may or may not be interrelated with respect to data set, experiment, or data acquisition system, can be inputted by a user (e.g., via application module 110) and stored in a short-term or long-term memory of system 100 (e.g., in storage module 150, a memory of instrument gateway module 120, a memory of analysis engine module 130, a memory of interface module 140, or a memory of a client, such as a user terminal or data acquisition system). In some embodiments, system 100 may transmit or execute a client request from a plurality of different clients at the same time. For example, system 100 may transmit client requests from a plurality of clients to the single instrument to be executed together or sequentially (e.g., if the client requests each comprise one or more similar aspect such as a similar experiment design), regardless of when the client requests were received from the client, whether the client requests pertain to the same experiment, or whether the client requests will produce or use the same data set(s) in when the data set(s) are collected/produced, analyzed, or displayed. By regulating and grouping or batching a plurality of client requests or one or more portion of a plurality of client requests, it is possible to increase computational efficiency and efficiency of data acquisition system usage.

Figure 4:
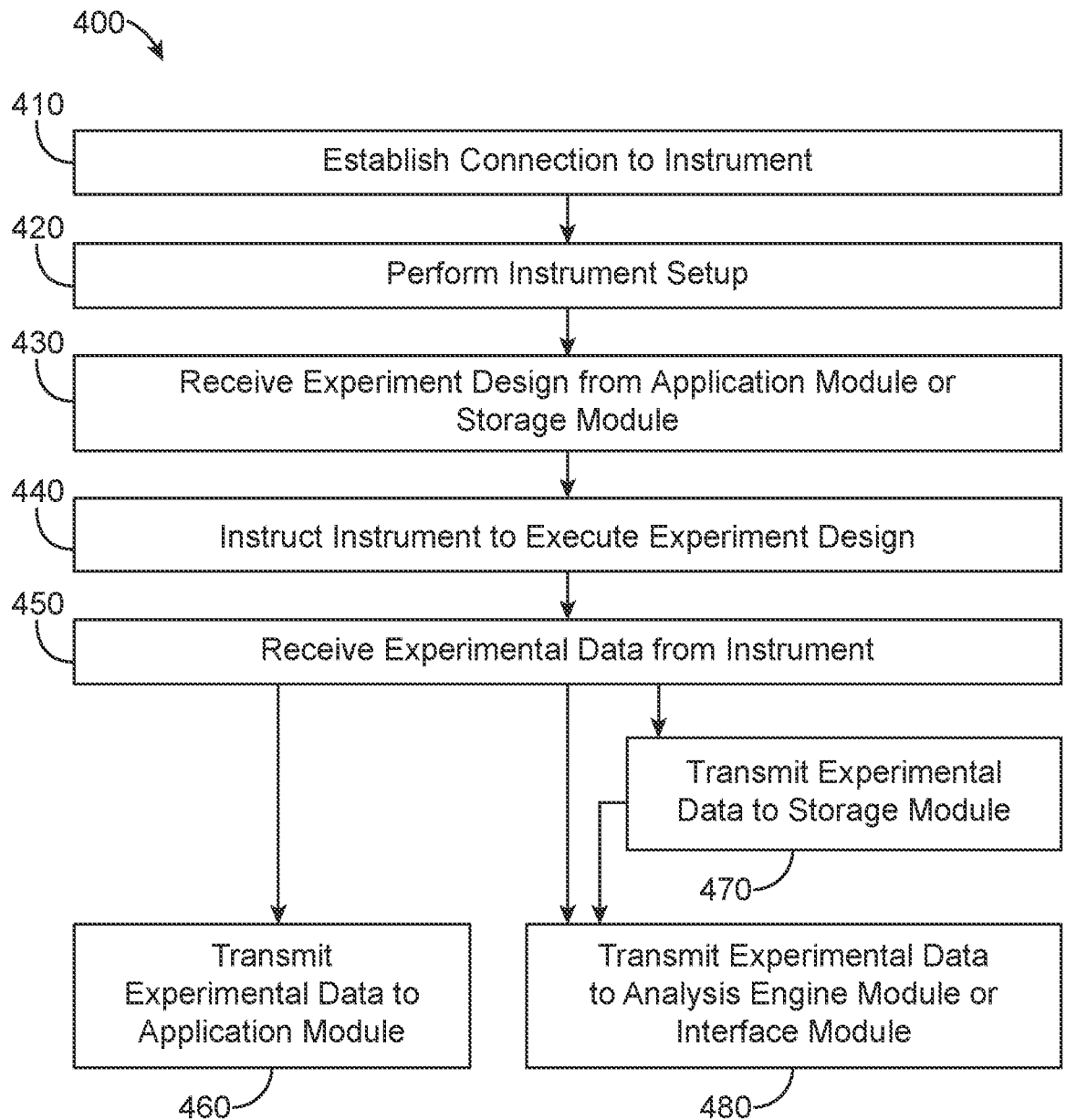
FIG. 4 shows a flow diagram of a method for the integrated operation of an instrument in the high-throughput phenotypic analysis of cellular assay data in accordance with one or more embodiments disclosed herein.

Turning now to FIG. 4, process 400 represents embodiments of the operation of system 100 wherein an instrument (e.g., a data acquisition system) is utilized in the creation of a data set. In a step 410, the instrument may be connected to system 100, and system 100 may initiate an instrument setup protocol in a step 420. During instrument setup, data may be transmitted from instrument set-up subsystem 124 to the instrument and/or data may be received from the instrument by instrument set-up subsystem 124. Data transmitted or received during a step 420 may comprise an environmental condition or parameter and/or instrument status information, which can include, for example, one or more instrument error message or information pertaining to instrument availability and scheduling). Instructions regarding experiment design may be received by experiment gateway module 120 from the application module 110 or from storage module 150 in a step 430 (e.g., as part of a client request or as automatically selected by system 100 as the result of a selection or preference indicated in a client request such as the selection of one or more specific type of analyzed data to be collected from a specific set of specimens) and may be transmitted to the instrument at a step 440. Transmission of one or more experimental design to the instrument may be accompanied by or followed by instructions to execute the experiment design and collect one or more data set (e.g., experimental data). In a step 450, data may be received from the instrument by a subsystem of gateway module 120. For example, image data (e.g., as part of an experimental data set) may be received by image ingest subsystem 122, and data related to the status of the data stream or the status of the instrument may be received by instrument monitoring subsystem 126. Received data (e.g., raw experimental data) may be transmitted to application module 110 for display in real-time, near real-time, or batch mode in a step 460. Data may also or may instead be transmitted to storage module 150, interface module 140, analysis engine module 130, or any combination thereof (e.g., for storage, transmission to a computational tool 104 or an additional data acquisition tool 106, or analysis).

In some embodiments, data received by instrument gateway module 120 can be stored in both short-term and long-term memory. For example, raw image data received from an instrument may be transmitted to a short-term memory cache to be displayed with extracted features and/or classification data after one or more analysis task has been completed, and it may also be transmitted to a long-term memory for long-term (e.g., cold) storage (e.g., storage module 150). In some embodiments, the data stored in a short-term cache may be of high, intermediate, or low quality or resolution in order to reduce the amount of memory required. In some embodiments, data may be transmitted to and stored in a long-term storage memory in its highest resolution and/or quality.

Figure 5:
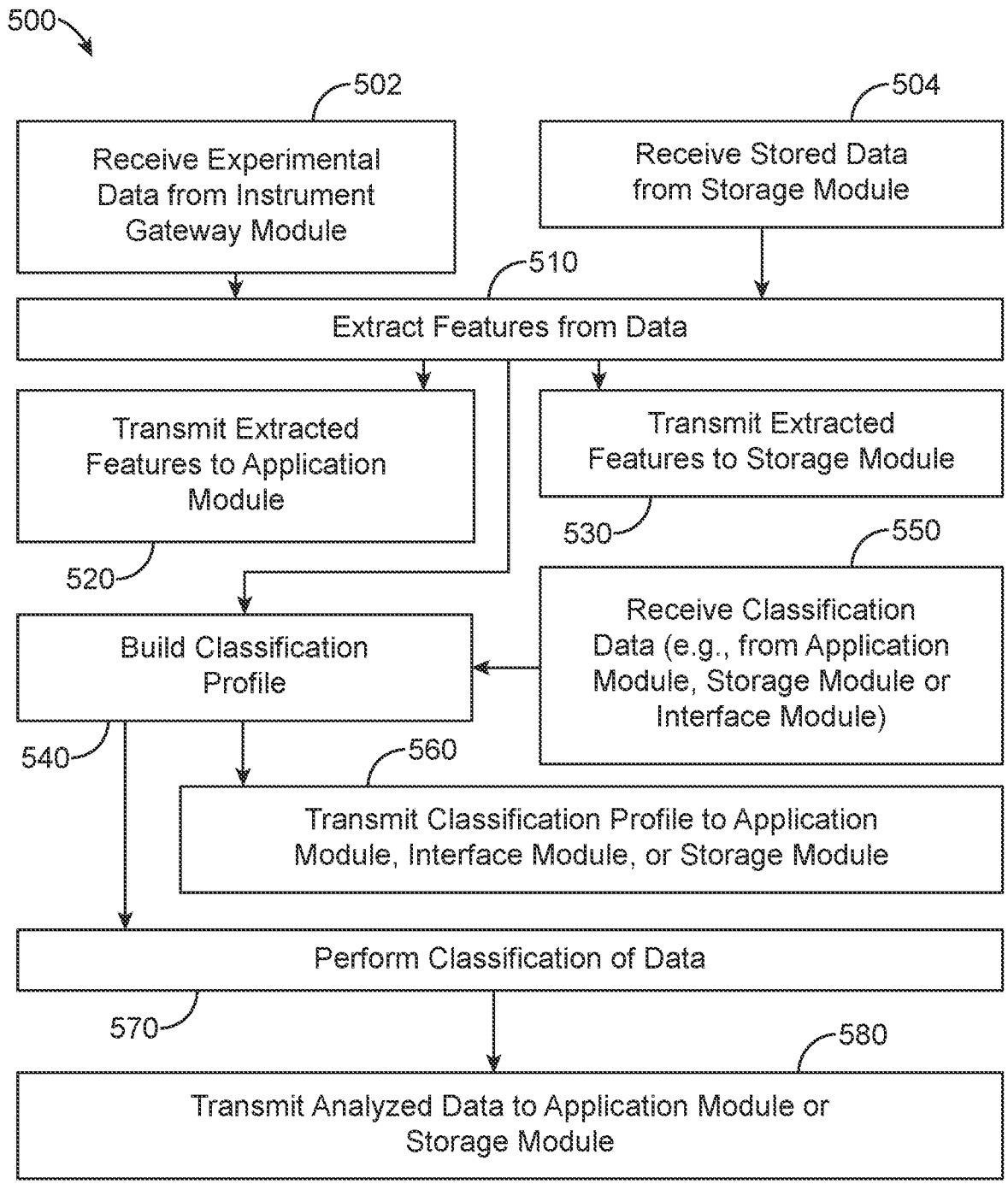
FIG. 5 shows a flow diagram of a method for integrated high-throughput analysis of phenotypic cellular assay data in accordance with one or more embodiments disclosed herein.

Referring now to FIG. 5, process 500 may be performed by system 100 for the purpose of analyzing data collected or stored by system 100. As described herein, analysis of data, which can comprise feature extraction and/or classification, can be performed in real-time, near real-time, or batch mode. Analysis of data in batch mode may be advantageous or necessary, for example, because batch mode processing can reduce the computational cost of analysis. Experimental data can be received by analysis engine module 130 (e.g., in image processing subsystem 132) from instrument gateway module 120 (e.g., from image ingest subsystem 122) in a step 502. Stored data to be analyzed can be received from storage module 150 (e.g., from image cache subsystem 156) in a step 504. Feature data (e.g., data comprising a feature data set) can be extracted from data received in step 502 or 504 by feature extraction subsystem 134 at a step 510. Extracted feature data may be transmitted to application module 110 for display or storage module 150 for storage in steps 520 and 530, respectively. Extracted feature data may be compiled into one or more classification data set and may be used by classification subsystem 136 to build (e.g., create, compile, or modify) a classification profile in a step 540. Classification data and/or extracted feature data may be received from application module 110, interface module 140 (e.g., as transmitted to the interface module or a subsystem thereof by a computational tool 104 or additional data acquisition tool 106), and/or storage module 150 in step 550 for the purpose of building a classification profile as well. In some embodiments, classification data transmitted in step 550 may be accompanied by a set of training data (e.g., in order to build one or more classification profile, as in step 540). A classification profile may optionally be transmitted to application module 110, interface module 140, or storage module 150 in a step 560. In some embodiments, building of a classification profile is unnecessary (e.g., when an existing classification profile is selected or supplied by the user), and one or more of steps 540, 550, or 560 may be omitted from process 500. Building a classification profile, as in a step 540, can comprise modifying an existing classification profile, which can comprise adding to, modifying, or deleting data from one or more classification data set from which the classification profile was originally built. In some embodiments, newly extracted feature data may be incorporated into one or more classification data set by analysis engine module 130 or a subsystem thereof. In a step 570, a data set (e.g., a feature data set) can undergo classification analysis wherein one or more functional or phenotypic characteristic may be ascribed to or associated with a data set or experimental group. In some embodiments, data pertaining to one or more functional or phenotypic characteristic of a data set or experimental group can comprise a classification result. A classification result can be produced by the application of one or more classification profile, which can, in turn, comprise user-defined classification data and/or classification data produced by supervised or unsupervised machine learning techniques. In a step 580, analyzed data, which may comprise a portion of a classification data set and/or one or more classification result, can be transmitted to application module 110 and/or storage module 150.

Figure 6:
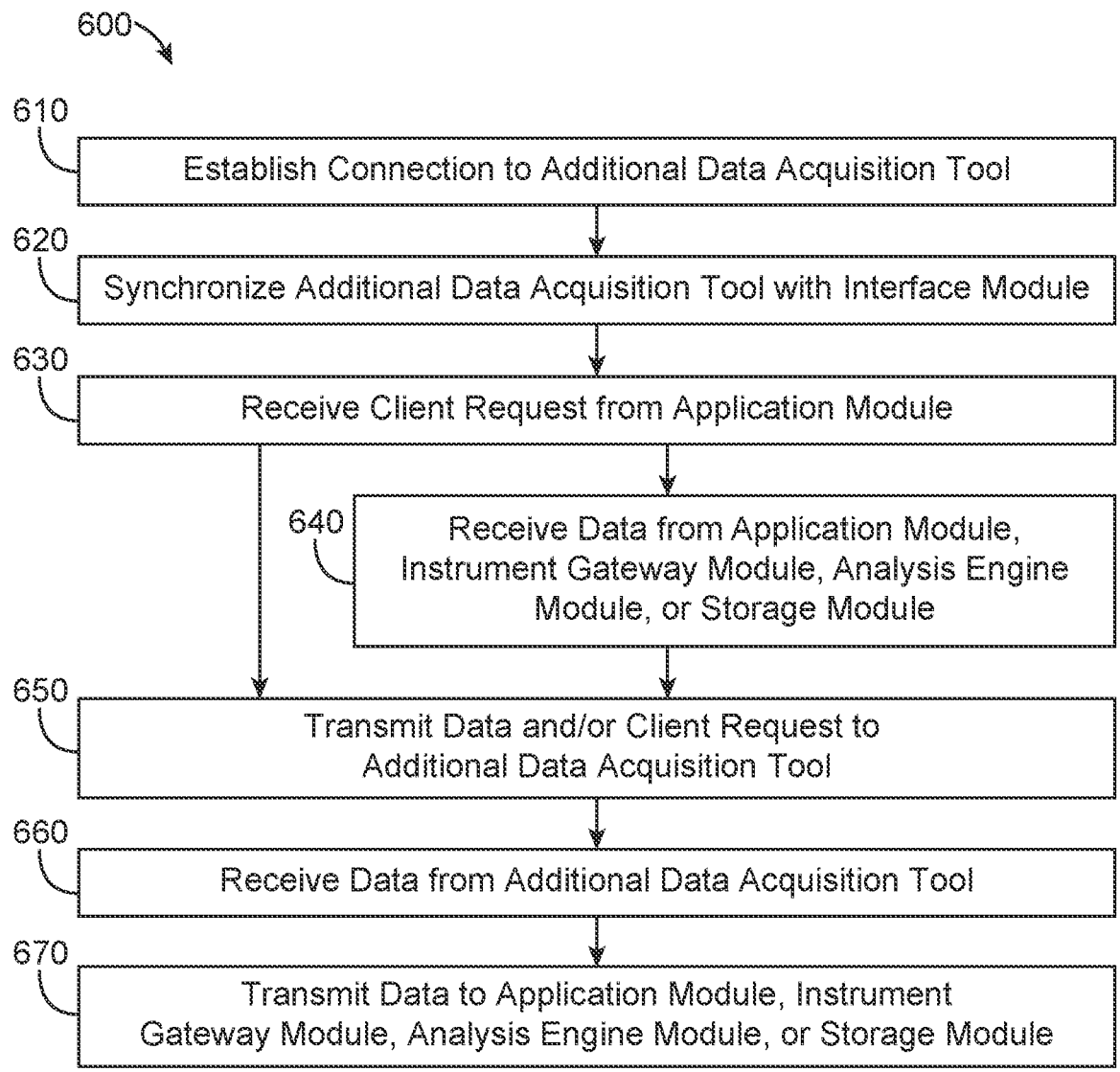
FIG. 6 shows a flow diagram of a method for high-throughput analysis of phenotypic cellular assay data involving integration of an additional data acquisition tool in accordance with one or more embodiments disclosed herein.

FIG. 6 illustrates an embodiment of process 600 wherein data is transferred between platform system 101 and a computational tool 104 or an additional data acquisition tool 106 via interface module 140. In a step 610, a connection can be established between platform system 101 and the additional data acquisition tool 106 or computational tool 104. The computational tool 104 or additional data acquisition tool 106 can be synchronized with interface module 140 at step 620. Synchronization of the additional data acquisition tool with interface module 140 at step 620 may comprise transmission of data from the computational tool 104 or additional data acquisition tool 106 to storage API subsystem 146 or vice versa. A client request may be received at step 630, for example, instructing an experiment comprising one or more imaging event to be performed using an additional data acquisition tool 106 or instructing one or more computational tool 104 or one or more additional data acquisition tool 106 to perform a data analysis procedure. In an optional step 640, additional data may be received by interface module from another module or subsystem of platform system 101 concurrently or following step 630. Data and/or a client request can be transmitted to one or more computational tool 104 or one or more additional data acquisition tool 106 in a step 650. In a step 660, data can be received from one or more computational tool 104 or one or more additional data acquisition tool 106 by one or more of the subsystems of interface module 140, depending on what data is transmitted. At step 670, data may be transmitted to application module 110 for display, instrument gateway module for image ingest, analysis engine module 130 for feature extraction and/or classification, and/or storage module 150 for storage.

Figure 7:
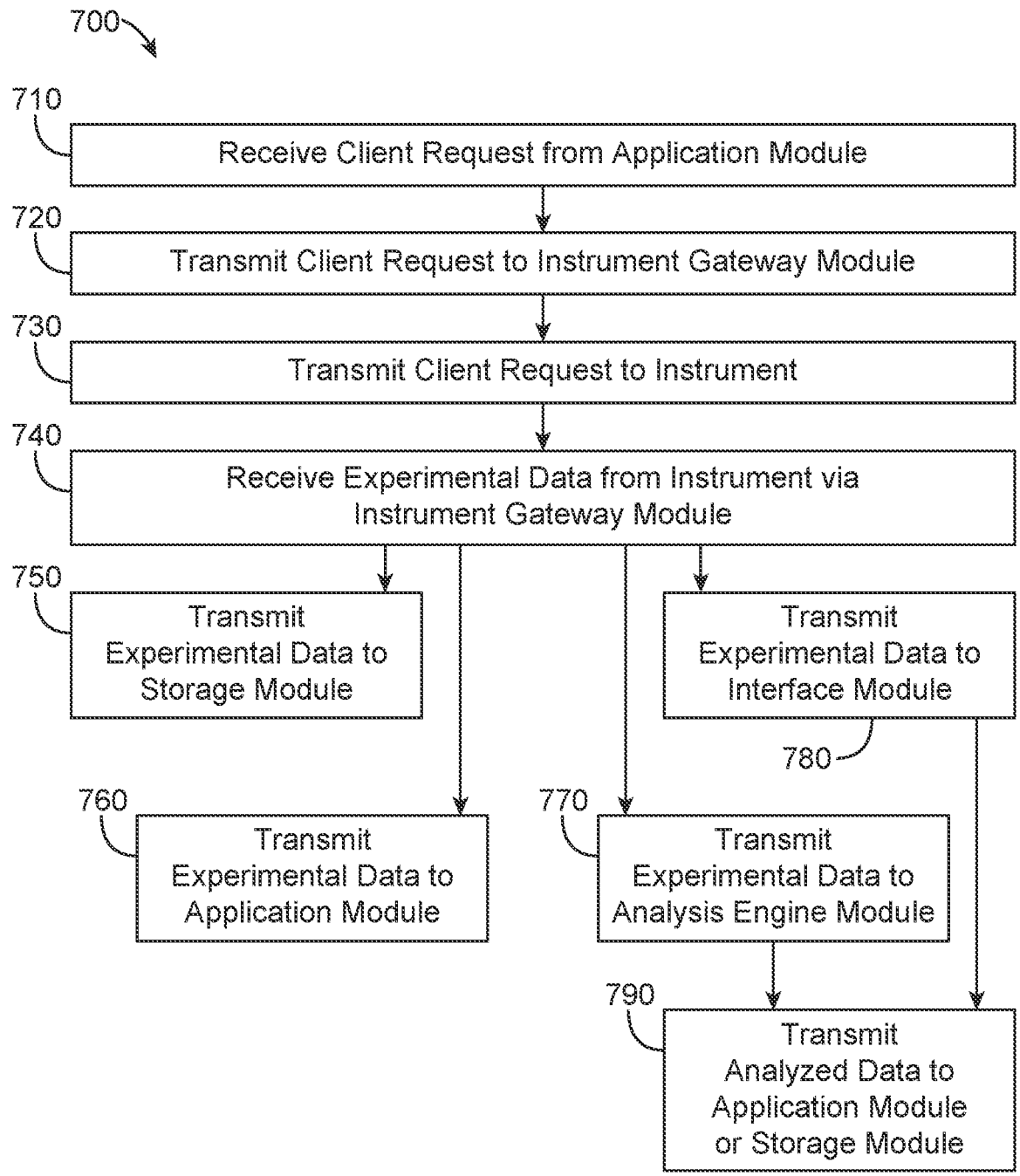
FIG. 7 shows a flow diagram of a method for integrated high-throughput analysis of phenotypic assay data in accordance with one or more embodiments disclosed herein.

Referring now to FIG. 7, process 700 illustrates an embodiment of the operation of system 100, wherein experimental data is acquired, analyzed, and displayed. In a step 710, a client request can be received from application module 110 (e.g., from user terminal 102). The client request can be transmitted to instrument gateway module 120 in a step 720, which can, in some embodiments, include transmission of an experiment design from application module 110 to instrument gateway module 120 as well. In a step 730, the data passed to instrument gateway module 120 can be transmitted to an instrument. In some embodiments, the instrument to which data is transmitted in step 730 is a computational tool 104 or an additional data acquisition tool 106, in which case data transmission may be routed through interface module 140, and in some embodiments, the instrument is not a computational tool 104 or an additional data acquisition tool 106. In step 740, experimental data, such as image data, can be received by instrument gateway module 120. If one or more instrument with which the experimental data was produced is an additional data acquisition tool 106, a portion of the data may be routed to instrument gateway module 120 via interface module 140. In a step 750, experimental data may be transmitted to storage module 150 for storage. In a step 760, the experimental data can be transmitted to application module 110 for display (e.g., in real-time, near real-time, or batch display mode). Experimental data can also be transmitted to analysis engine module 130 for analysis (e.g., feature extraction and/or classification) in a step 770. Optionally, experimental data can be transmitted to interface module 140 in step 780 for transmission to a computational tool 104 or an additional data acquisition tool 106 and subsequent data analysis by the additional data acquisition tool. Following step 770 (e.g., or step 780 and subsequent receipt of analyzed data from a computational tool 104 or an additional data acquisition tool 106 via interface module 140), analyzed data can be transmitted to application module 110 for display or to storage module 150 for storage.

The specific steps, their order, and the order of processes 300, 400, 500, 600, and 700 may be defined by a stored or custom experiment design and/or by additional selections or preferences inputted by a user. As such, one or more of processes 300, 400, 500, 600, or 700 may comprise additional steps, different steps, fewer steps, in accordance with embodiments of the systems, methods, and devices disclosed herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A system for the classification of one or more specimens, the system comprising:
    a controller configured to:
        interface with one or more instruments through an instrument gateway module configured to receive a plurality of experimental data sets from the one or more instruments, wherein the plurality of experimental data sets is produced during a plurality of experiments; wherein the one or more instruments comprise a multi-spectral imager for fluorescence and bright field detection;
        extract one or more feature data sets from the plurality of experimental data sets;
        store at least a portion of the one or more feature data sets in a long-term data storage subsystem;
        store at least a portion of the one or more feature data sets or at least a portion of the plurality of experimental data sets in a short-term storage cache;
        build one or more classification profiles based on a classification data set comprising at least a portion of the one or more feature data sets; and
        classify one or more specimens of an experiment of the plurality of experiments using the one or more classification profiles, wherein the controller receives the plurality of experimental data sets before the classifying is performed on any of the experimental data sets.

2. The system of claim 1, wherein the classification data set comprises at least a portion of each feature data set of a plurality of feature data sets, wherein a first portion of each feature data set is produced from a first experimental data set of the plurality of experimental data sets and a second portion of each feature data set is produced from a second experimental data set of the plurality of experimental data sets.

3. The system of claim 2, wherein the first experimental data set comprises data from a different experiment of the one or more plurality of experiments than the data of the second experimental data set, the plurality of experiments comprising 100, 200, 500, 1,000, 5,000, 10,000, or 100,000 different experiments.

4. The system of claim 2, wherein at least a portion of the first experimental data set is received from a different instrument of the one or more instruments than the second experimental data set.

5. The system of claim 1, wherein the controller receives the plurality of experimental data sets before the extracting is performed on any of the experimental data sets.

6. The system of claim 1, wherein the one or more specimens comprises 100, 150, 200, 500, 1,000, 2,500, 5,000, 7,500, or 10,000 different specimens and the classification of the one or more specimens comprises categorizing the one or more specimens based on one or more feature data sets.

7. The system of claim 1, wherein building the classification profile comprises supervised machine learning or unsupervised machine learning.

8. The system of claim 1, wherein classification results are determined from the classification of one or more specimens of an experiment of the plurality of experiments using the classification profile.

9. The system of claim 1, wherein the controller is further configured to display an analysis data set comprising at least a portion of the experimental data sets, at least a portion of the one or more feature data sets, or at least a portion of the classification data set, wherein the analysis data set is displayed in real-time, near-real time, or batch mode.

10. The system of claim 1, wherein the one or more specimens comprises one or more colonies of microbial cells.

11. A method for the classification of one or more specimens, the method comprising:
    receiving a plurality of experimental data sets from one or more instruments, wherein the plurality of experimental data sets is produced during a plurality of experiments; wherein the one or more instruments comprise a multi-spectral imager for fluorescence and bright field detection;
    extracting one or more feature data sets from the plurality of experimental data sets;
    storing at least a portion of the one or more feature data sets in a long-term data storage subsystem;
    storing at least a portion of the one or more feature data sets or at least a portion of the plurality of experimental data sets in a short-term storage cache;
    building one or more classification profiles based on a classification data set comprising at least a portion of the one or more feature data sets; and
    classifying one or more specimens of an experiment of the plurality of experiments using the one or more classification profiles, wherein the plurality of experimental data sets is received before the classifying is performed on any of the experimental data sets.

12. The method of claim 11, wherein the classification data set comprises at least a portion of each feature data set of a plurality of feature data sets, wherein a first portion of each feature data set is produced from a first experimental data set of the plurality of experimental data sets and a second portion of each feature data set is produced from a second experimental data set of the plurality of experimental data sets.

13. The method of claim 12, wherein the first experimental data set comprises data from a different experiment of the plurality of experiments than the data of the second experimental data set, the plurality of experimental data sets comprising data from 100, 200, 500, 1,000, 5,000, 10,000, or 100,000 experiments.

14. The method of claim 12, wherein at least a portion of the first experimental data set is received from a different instrument of the one or more instruments than the second experimental data set.

15. The method of claim 11, wherein the plurality of experimental data sets is received before the extracting is performed on any of the experimental data sets of the plurality of experimental data sets.

16. The method of claim 11, wherein the one or more specimens comprises 100, 150, 200, 500, 1,000, 2,500, 5,000, 7,500, or 10,000 different specimens and the classification of one or more specimens comprises categorizing the one or more specimens based on one or more feature data sets.

17. The method of claim 11, wherein building the classification profile comprises supervised machine learning or unsupervised machine learning.

18. The method of claim 11, wherein classification results are determined from the classification of one or more specimens of an experiment of the plurality of experiments using the classification profile.

19. The method of claim 11, further comprising displaying an analysis data set comprising at least a portion of the plurality of experimental data sets, at least a portion of the one or more feature data sets, or at least a portion of the classification data set, wherein the analysis data set is displayed in real-time, near-real time, or batch mode.

20. The method of claim 11, wherein the one or more specimens comprises one or more colonies of microbial cells.

\* \* \* \* \*